United States Patent [19]

Malabarba et al.

[11] Patent Number: 4,954,483
[45] Date of Patent: Sep. 4, 1990

[54] CARBOXYLIC ACID ESTER DERIVATIVES OF DEGLUCOTEICOPLANIN

[75] Inventors: Adriano Malabarba, Milan; Paolo Strazzolini, Fiume Veneto; Aldo Trani, Milan; Ambrogio Magni, Osnago; Bruno Cavalleri, Milan, all of Italy

[73] Assignee: Gruppo Lepetit, S.p.A., Italy

[21] Appl. No.: 243,168

[22] PCT Filed: Jun. 2, 1985

[86] PCT No.: PCT/EP85/00262
§ 371 Date: Feb. 6, 1986
§ 102(e) Date: Feb. 6, 1986

[87] PCT Pub. No.: WO86/00075
PCT Pub. Date: Jan. 3, 1986

Related U.S. Application Data

[63] Continuation-in-part of Ser. No. 131,245, Dec. 7, 1987, abandoned, which is a continuation of Ser. No. 839,320, filed as PCT EP85/00262 on June 2, 1985, published as WO86/00075 on Jan. 3, 1986.

[30] Foreign Application Priority Data

Jun. 13, 1984 [GB] United Kingdom ............... 8415092

[51] Int. Cl.$^5$ ............... A61K 37/02; C07K 7/50; A23K 1/00
[52] U.S. Cl. ............... 514/9; 530/317; 426/635
[58] Field of Search ............... 514/9; 530/317; 426/635

[56] References Cited

U.S. PATENT DOCUMENTS

| | | | |
|---|---|---|---|
| 4,322,343 | 3/1982 | Debono | 514/8 |
| 4,495,179 | 1/1985 | Hoehn et al. | 514/9 |
| 4,497,802 | 2/1985 | Debono | 514/8 |
| 4,629,781 | 12/1986 | Strazzolini et al. | 530/317 |

FOREIGN PATENT DOCUMENTS

| | | |
|---|---|---|
| 0090578 | 10/1983 | European Pat. Off. |
| 0100605 | 2/1984 | European Pat. Off. |
| 0132116 | 1/1985 | European Pat. Off. |
| 2121401 | 12/1983 | United Kingdom |
| 2148303 | 5/1985 | United Kingdom |

OTHER PUBLICATIONS

Barna et al., J. Am. Chem. Soc., vol. 106, No. 17, pp. 4895–4902 (8/22/1984).
Hunt et al., J. Am. Chem. Soc., vol. 106, pp. 4891–4895 (8/22/1984).
Barna et al., The Journal of Antibiotics, vol. 37, pp. 1204–1208 (Oct. 1984).
Malabarba et al., The Journal of Antibiotics, vol. 37, pp. 988–999 (Sep., 1984).

*Primary Examiner*—Lester L. Lee
*Assistant Examiner*—Christina Chan

[57] ABSTRACT

The present invention is directed to carboxylic acid esters of deglucoteicoplanin, i.e. of the aglycon moiety of the antibiotic teicoplanin. The compounds of the invention are conveniently prepared either by deglucoteicoplanin or by any of the glycopeptides of the teicoplanin group, such as teicoplanin itself, one of its components, antibiotic L 17054 and antibiotic L 17046.

15 Claims, No Drawings

CARBOXYLIC ACID ESTER DERIVATIVES OF DEGLUCOTEICOPLANIN

This is a continuation-in-part of application Ser. No. 131,245, filed Dec. 7, 1987 now abandoned which is a continuation of application Ser. No. 839,320 filed as PCT EP85/00262 on Jun. 2, 1985, published as WO86/00075 on Jan. 3, 1986, now abandoned.

The present invention is directed to derivatives of the peptidic moiety of the antibiotic substance called teicoplanin of the following formula I

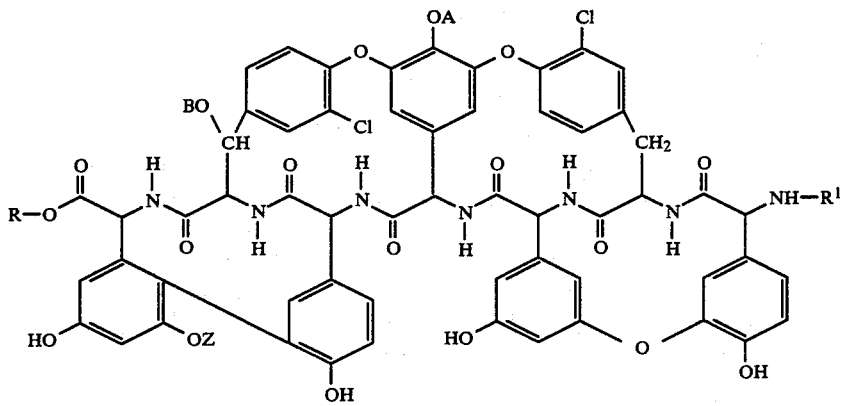

wherein

R represents $(C_1-C_{12})$alkyl, hydroxy$(C_1-C_{12})$alkyl, $(C_1-C_3)$alkoxy$(C_1-C_{12})$alkyl, halo$(C_1-C_{12})$alkyl; a group of formula

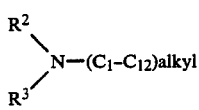

wherein $R^2$ and $R^3$ each independently represents hydrogen or $(C_1-C_4)$alkyl groups, or $R^2$ and $R^3$ taken together with the adjacent nitrogen atom represent a 5–7 membered aromatic, partially hydrogenated or saturated heterocycle ring which may optionally contain a further heteroatom selected from S, O and N; a group of formula

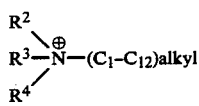

wherein $R^2$ and $R^3$ are as defined above and $R^4$ represents hydrogen or $(C_1-C_4)$alkyl; or R represents a group of formula

wherein m represents the integer 2 or 3, n is an integer from 1 to 10, and one of the hydrogen atoms of the —$(CH_2)$—group may be substituted by a methyl group; $(C_2-C_{10})$ alkanoyloxymethyl, phenyl, substituted phenyl, phenyl$(C_1-C_6)$alkyl, substituted phenyl$(C_1-C_6)$alkyl, $R^1$ represents hydrogen or an amino-protecting group, A, B, and Z each individually represents a hydrogen group, and the pharmaceutically-acceptable acid addition salts thereof.

As used herein the term "alkyl" includes both straight and branched hydrocarbon groups; more particularly, "$(C_1-C_{12})$alkyl" represents a straight or branched aliphatic hydrocarbon chain of 1 to 12 carbon atoms such as methyl, ethyl, propyl, 1-methylethyl, butyl, 1-methylpropyl, 1,1-dimethylethyl, pentyl, 1-methylbutyl, 2-methylbutyl, 1-hexanyl, 2-hexanyl, 3-hexanyl, 3,3-dimethyl-1-butanyl, 4-methyl-1-pentanyl; 3-methyl-1-pentanyl, 2,2-dimethyl-3-pentanyl, 2,4-dimethyl-3-pentanyl, 4,4-dimethyl-2-pentanyl, 5-methyl-2-hexanyl, 1-heptanyl, 2-heptanyl, 5-methyl-1-hexanyl, 2-ethyl-1-hexanyl, 2-methyl-3-hexanyl, 1-octanyl, 2-octanyl, 2-cyclopentylethanyl, 1-nonanyl, 2-nonanyl, 1-decanyl, 2-decanyl and 3-decanyl, 1-undecyl, 2-dodecyl and the like, while "$(C_1-C_4)$alkyl" represents a straight or branched hydrocarbon chain of 1 to 4 carbon atoms; the term "$(C_1-C_3)$alkoxy" represents an alkoxy group of 1 to 3 carbon atoms, i.e. methoxy, ethoxy, n-propyloxy, isopropyloxy.

The term "$(C_2-C_{10})$alkanoyloxymethyl" refers to alkanoyloxymethyl group wherein the alkanoyl portion is represented by a straight or branched alkanoyl group of 2 to 10 carbon atoms.

Representative examples of $(C_2-C_{10})$alkanoyloxymethyl groups are: acetyloxymethyl, n-propionyloxymethyl, butyryloxymethyl, 2-methylpropanoyloxymethyl, pentanoyloxymethyl, 2-methylbutanoyloxymethyl, hexanoyloxymethyl, 3-methylpentanoyloxymethyl, 2,2-dimethylpropanoyloxymethyl, pivaloyloxymethyl, 3,3-dimethylbutanoyloxymethyl, 2,2-dimethylpentanoyloxymethyl, and the like. Examples of "5–7 membered aromatic, partially hydrogenated or saturated heterocycle ring" according to the invention are: pyrrolyl, pyridyl, pyrrolidinyl, pyridinyl, piperazinyl, imidazolyl, pyrimidinyl, pyridazyl, oxazolyl, oxazolidinyl, imidazolinyl, pyrazolidinyl, thiazolyl, thiazolinyl, thiazolidinyl, azepinyl, diazepinyl and thiazepinyl and the like.

The term "halo$(C_1-C_{12})$alkyl" represents mono- or poly-halogenated alkyl group of 1 to 12 carbon atoms wherein the halo atom is chloro, fluoro or bromo.

Examples of halo$(C_1-C_{12})$alkyl groups are: monochloroethyl, dichloroethyl, trichloroethyl, dichlorofluoroethyl, difluorochloroethyl, difluoroethyl, trifluoroethyl, dichloropropyl, 1,1,1,3,3,3-hexafluoro-2-propyl, monochlorobutyl, difluorobutyl or trifluorobutyl and tetrafluorobutyl, and the like.

The term "β-poly-halo($C_1$-$C_{12}$)alkyl" refers in particular to halo($C_1$-$C_{12}$)alkyl derivatives having at least a halogen atom in the position-β of the alkyl chain.

The term "substituted phenyl" indicates a phenyl residue which is substituted with one or two substituents selected from chloro, bromo, iodo, ($C_1$-$C_4$)alkyl, hydroxy, ($C_1$-$C_4$)alkoxy, ($C_1$-$C_4$)alkylthio, nitro, and trifluoromethyl.

Examples of phenyl substituted alkyl groups are: benzyl, m-chlorobenzyl, o-fluorobenzyl, m-fluorobenzyl, p-fluorobenzyl, m-methylbenzyl, m-methoxybenzyl, o-ethoxybenzyl, m-butoxybenzyl, p-tert.butoxybenzyl, p-tert.butylbenzyl, phenethyl, p-chlorophenethyl, m-chlorophenetyl, o-methoxyphenethyl, m-methoxyphenethyl, o-propylphenethyl, o-ethoxyphenethyl, p-fluorophenethyl, p-bromophenethyl, o-propoxyphenethyl, o-butoxyphenethyl, 1-(p-isopropylphenyl)ethyl, 3-phenyl-1-propyl, 2-phenyl-1-propyl, 4-phenyl-1-butyl and 3-phenyl-1-butyl and the like.

The terms "teicoplanin nucleus", "deglucoteicoplanin", "teicoplanin aglycone moiety", "deglucoteicoplanin moiety" refer to the heptapeptidic residue of the antibiotic substance named teicoplanin and can be represented by the above formula I wherein R and $R^1$ are hydrogen atoms, and A, B and Z each individually represents a hydrogen group.

The compounds of formula I possess a basic function which is capable of forming salts and therefore they can be transformed into their pharmaceutically acceptable acid-addition salts according to procedures known per se in the art.

Representative and suitable acid addition salts of the compounds of formula I include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and like acids.

The transformation of the free amino compounds of the invention into the corresponding acid addition salts, and the reverse, i.e. the transformation of an acid addition salt of a compound of the invention into the non-salt or free amino form, are within the ordinary technical skill and are encompassed by the present invention.

In view of the similarity of the properties of the compounds of formula I and their salts, what is said in the present application when dealing with the biological activities of the compounds of formula I applies also to their pharmaceutically acceptable salts, and vice versa.

As is true with any group of compounds exhibiting biological activity, certain species of compounds are preferred. Of those compounds of formula I, applicants prefer those compounds wherein $R_1$ is hydrogen as well as those compounds of formula I wherein R represents a methyl or ethyl group, a benzyl group, an hydroxy($C_1$-$C_4$)alkyl group, especially an hydroxymethyl or hydroxyethyl group, or a halo($C_1C_4$)alkyl group, especially a halomethyl or haloethyl group. The most preferred compounds, are those compounds of formula I wherein R represents a benzyl, methyl, hydroxyethyl, bromoethyl, chloroethyl, or fluoroethyl group.

The compounds of the invention are useful as semisynthetic antibacterial agents or as intermediates to such agents. They are derivatives of the agluco-nucleus of the teicoplanin antibiotics; more particularly, the compounds of the present invention are ester derivatives at the carboxy function of the teicoplanin aglycone moiety, (i.e. deglucoteicoplanin esters), N-protected deglucoteicoplanin or N-protected deglucoteicoplanin esters. All these compounds possess antimicrobial activity; however, the N-protected deglucoteicoplanin and N-protected deglucoteicoplanin ester derivatives are mainly useful as intermediates to the antimicrobially active deglucoteicoplanin esters.

Teicoplanin is the international non-proprietary name (INN) of the antibiotic substance formerly named teichomycin which is obtained by cultivating the strain *Actinoplanes teichomyceticus* nov.sp. ATCC 31121 in a culture medium containing assimilable sources of carbon, nitrogen and inorganic salts (see U.S. Pat. No. 4,239,751). According to the procedure described in the above cited patent an antibiotic complex containing Teichomycin $A_1$, $A_2$ and $A_3$ is recovered from the separated fermentation broth by extraction with a suitable water insoluble organic solvent and precipitation from the extracting solvent according to common procedures. Teichomycin $A_2$, which is the major factor of the isolated antibiotic complex, is then separated from the other factors by means of column chromatography on Sephadex ®.

British Patent Application Publication No. 2121401 discloses that antibiotic Teichomycin $A_2$ actually is a mixture of five closely related co-produced main components.

According to recent structural studies it is possible to represent teicoplanin $A_2$ (formerly Teichomycin $A_2$) main components 1, 2, 3, 4 and 5 by the above formula I wherein R and $R^1$ are hydrogen, A is N-[($C_{10}$-$C_{11}$)aliphatic acyl]-β-D-glucosaminyl group, B is a N-acetyl-β-D-glucosaminyl group and Z is an α-D-mannosyl group. All these sugar moieties, when present, are linked to the teicoplanin nucleus through O-glycosidic bonds.

In addition, it has been found that it is possible to transform teicoplanin, a pure factor thereof or a mixture of any of said factors in any proportion, into unitary antibiotic products by means of selective hydrolysis of one or two sugar moieties. They are named antibiotic L 17054 and antibiotic L 17046 and are described in European Patent Application Publication No. 0119575 and European Patent Application Publication No. 0119574, respectively.

Preferred hydrolysis conditions for the production of antibiotic L 17054 are: about 0.5 N hydrochloric acid at a temperature between 70° and 90° C. and for a time which is generally between 15 and 90 min.

Antibiotic L 17054 is represented by the above formula I wherein R and $R^1$ are hydrogen atoms, and A is a hydrogen group, B is N-acetyl-β-D-glucosaminyl and Z is α-D-mannosyl wherein the sugar moieties are linked to the peptidic nucleus through an O-glycosidic bond.

Preferred hydrolysis conditions for the preparation of antibiotic L 17046 are: about 1-3 N hydrochloric acid, at a temperature between 50° and 90° C. and for a time which is generally between 30 and 60 min.

Antibiotic L 17046 is represented by the above formula I wherein R and $R^1$ are hydrogen atoms, A and Z each individually represents a hydrogen group, and B is N-acetyl-β-D-glucosaminyl wherein the sugar moiety is linked to the peptidic nucleus through an O-glycosidic bond.

The complete selective cleavage of all the sugar moieties of the teicoplanin compounds gives an aglycone molecule which is called antibiotic L 17392, or deglucoteicoplanin, and is represented by the above formula I wherein R and R¹ are hydrogen atoms, and A, B, and Z each individually represents a hydrogen group.

A substance having the same structural formula is disclosed in European Patent Application Publication No. 0090578 and is named antibiotic A 41030 factor B. This substance is obtained by means of a microbiological process which involves the fermentation of the strain *Streptomyces virginiae* NRRL 12525 or *Streptomyces virginiae* NRRL 15156 in a suitable medium, the isolation, purification and separation into its components of antibiotic A 41030, an antibiotic complex of at least seven factors, antibiotic A 41030 factor B, included.

All the above named compounds, i.e. teicoplanin, a teicoplanin factor, a mixture of any said factors in any proportion, antibiotic L 17054, antibiotic L 17046, antibiotic L 17392, are starting materials for the preparation of the ester derivatives of the invention. To facilitate the discussion, in the present specification any one of the above starting materials, i.e. teicoplanin complex as obtained according to U.S. Pat. No. 4,239,751, any further purification thereof, a compound of the above formula I wherein R and R¹ are hydrogen, A represents hydrogen or a [($C_{10}$–$C_{11}$)aliphatic acyl]-β-D-glucosaminyl, B represents hydrogen or a N-acetyl-β-D-glucosaminyl, and Z represents hydrogen or·α-D-mannosyl, or any mixture thereof in any proportion will be generally referred to as a "teicoplanin-like compound" or a "teicoplanin-like substance". Representative and preferred examples of ($C_{10}$–$C_{11}$)aliphatic acyl groups are n-decanoyl, 8-methylnonanoyl, Z-4-decenoyl, 8-methyldecanoyl, and 9-methyldecanoyl groups.

The deglucoteicoplanin esters of formula I are prepared by submitting a suitable teicoplanin-like substance to esterification under controlled conditions.

These esterification conditions depend on the nature of the specific teicoplanin-like substance which is used as the starting material and, to a certain extent, on the specific ester which is desired.

In general, the reaction conditions of the esterification procedure are such that the "teicoplanin nucleus" is not modified, and in case the substituents A, B and Z of the starting teicoplanin-like substance are not all hydrogen atoms, the reaction conditions of the esterification procedure are such that all the sugar moieties of the starting material are hydrolyzed before the main reaction is completed.

Therefore one object of the present invention is to provide a process for preparing a deglucoteicoplanin ester which comprises:
(a) submitting a teicoplanin-like substance characterized by having a free or activated carboxylic acid function to a controlled esterification procedure, and
(b) when the starting material comprises a compound of formula I wherein at least one of A, B and Z is a sugar moiety, providing a reaction medium capable of selectively hydrolyzing the sugar substituents of the teicoplanin nucleus without affecting either the teicoplanin nucleus or the newly formed carboxylic acid ester function.

It will be recognized by those skilled in the art that the teicoplanin-like substrates possess a free aminic function which may interfere with the reaction course and therefore that in some instances it will be necessary to protect this amino function before starting the esterification process.

The N-protecting group which may be used in the process of the present invention is one of the N-protecting groups known in the art such as those described in reference books (see for instance T. W. Greene, "Protective Groups in Organic Synthesis", John Wiley and Sons, New York, 1981, p. 323–326, and M. Mc. Omie "Protecting Groups in Organic Chemistry", Plenum Press, New York, 1973) and which is capable of forming a bond with the amino groups of the teicoplanin-like derivative which is stable at the conditions of the reaction process, does not unfavourably interfere with the main esterification reaction, and is easily cleavable and removable from the reaction media, without altering the newly formed deglucoteicoplanin ester bond, at the end of the reaction process.

Representative examples of N-protecting groups which may be advantageously used in the process of the invention are carbamate forming reagents characterized by the following oxycarbonyl groups: 1,1-dimethylpropynyloxycarbonyl, t-butyloxycarbonyl, vinyloxycarbonyl, allyloxycarbonyl, cinnamyloxycarbonyl, 4,5-diphenyl-3-oxazolin-2-one, benzyloxycarbonyl, p-nitrobenzyloxycarbonyl, 3,4-dimethoxy-6-nitrobenzyloxycarbonyl, 2,4-dichlorobenzyloxycarbonyl, 5-benzisoxazolylmethyloxycarbonyl, 9-anthrylmethyloxycarbonyl, diphenylmethyl oxycarbonyl, isonicotinyloxycarbonyl, S-benzyloxycarbonyl, and the like.

Other suitable N-protecting agents are aldehydes or ketones, or derivatives thereof which are capable of forming Shiff bases with the amino group of the teicoplanin nucleus to be protected.

Preferred examples of such Shiff bases forming agents, are benzylaldehydes and particularly preferred is 2-hydroxybenzylaldehyde (salicylaldehyde).

As it is appreciated by the skilled technician, the ultimate choice of the specific N-protecting group depends on the characteristics of the particular ester which is desired. In fact, this ester should be stable at the condition of removal of the N-protecting groups. Since the conditions of removal of the different N-protecting groups are known, the skilled technician is capable of selecting the proper protecting group. For instance, where a benzyl ester is desired, the N-protecting groups which are removable by catalytic hydrogenation, such as the benzyloxycarbonyl group, should be avoided, while those N-protecting groups which are removable under acidic conditions, such as t.butoxycarbonyl, can be conveniently used.

General procedures for preparing the compounds of the invention include therefore reacting a N-protected or free-amino teicoplanin-like substrate with an alcohol in an acidic medium, or a N-protected deglucoteicoplanin derivative with an alkyl halide (preferably bromide, chloride or iodide) as well as reacting a N-protected deglucoteicoplanin substrate having an activated carboxylic function with the selected alcohol.

The term "activated carboxylic function" means a derivatization of the carboxy function of the teicoplanin-like substrate which renders this carboxy function reactive to coupling with the alcohol reactive to form the ester bond which characterizes the compounds of the invention.

Preferred "activating agents" of the carboxylic function according to the invention, include carbonyldiimide derivatives, such as N,N'-dicyclohexylcarbodiimide, N,N'-diisopropylcarbodiimide, and the like, which are capable of giving a reactive intermediate which, because of its instability, is in general not isolated, but reacted in situ with the selected alcohol to form the desired ester.

More particularly, controlled esterification procedures useful for preparing the deglucoteicoplanin ester derivatives of the invention include esterification reactions which employ acidic alcoholic conditions either in the presence of a N-protected teicoplanin-like derivative or preferably in the presence of a free teicoplanin-like derivative; esterification reactions wherein the teicoplanin-like substrate is brought together with an excess of the selected alkanols, which has to be liquid at the reaction temperature, in the presence of concentrated hydrochloric acid, and wherein the reaction mixture is maintained under vacuum and from time to time a small amount of a solvent capable of forming minimum azeotropic mixtures with water is added thereto, and the resulting azeotrope is distilled off under reduced pressure; esterification reactions of a N-protected deglucoteicoplanin derivative with a suitable alcoholic substrate such as phenol or substituted phenol in the presence of a carbodiimide as the activating agent of the carboxy function; and esterification procedures wherein an alkali metal, silver or lead salt of a N-protected deglucoteicoplanin derivative in an inert organic solvent is reacted with a halogenide of formula R-X, wherein R is as previously defined but with the exclusion of the halogenoalkyl groups, and X is a chlorine or preferably bromine or iodine atom, optionally in the presence of a tertiary amine such as triethylamine, picoline and the like.

A general procedure for preparing esters of formula I wherein the alcoholic residue is a residue of a bulky alcohol which is a liquid at the reaction temperature and slightly water soluble or practically water insoluble, comprises, therefore, reacting a teicoplanin-like compound with a solution of the suitably selected alcohol in the presence of a mineral acid, preferably a hydrogen halide. The reaction temperature is preferably between 50° and 80° C. Preferred hydrogen halides are hydrogen bromide and hydrogen chloride with hydrogen chloride as the first choice.

Representative examples of esters of formula I which can be prepared by this procedure are the alkyl, ($C_1$–$C_3$)alkoxyalkyl, and haloalkyl esters wherein the alkyl chain is a straight or branched hydrocarbon chain of from 5 to 12 carbon atoms, phenyalkyl, substituted phenylalkyl esters, polyglycol esters having the alcoholic residue of formula

H—[O(CH$_2$)$_m$]—n wherein m is as above and n is as above but greater than 1, and polyoxyglycol monoalkylether esters having the alcoholic residue of formula

($C_1$–$C_3$)alkyl[O(CH$_2$)$_m$]—n wherein m and n are as previously defined.

The bulky alcohols that are preferably used in this process are therefore alcohol derivatives of formula ROH wherein R represents ($C_4$–$C_{12}$)alkyl, ($C_1$–$C_3$)alkoxy($C_1$–$C_{12}$)alkyl, with 4 or more carbon atoms, halo($C_4$–$C_{12}$)alkyl, phenyl($C_1$–$C_6$)alkyl, substituted phenyl($C_1$–$C_6$)alkyl, polyoxyglycols or the polyoxyglycol monoalkylethers as above defined with the exclusion of ($C_2$–$C_3$)glycols as hereinbelow defined.

Any of the above listed teicoplanin-like compounds and any mixture thereof can be used as the starting material according to this procedure.

Another general procedure for preparing esters of formula I wherein the alcoholic residue is a residue of an alcohol which is a liquid at the reaction temperature but with the exclusion of ($C_1$–$C_3$)alkanols, β-polyhalogeno($C_1$–$C_{12}$)alkanols, phenol, substituted phenols as defined above, ($C_2$–$C_3$)glycols, i.e., those glycols of formula ROH wherein R represents a group of formula

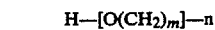
H—[O(CH$_2$)$_m$]—n wherein m is 2 or 3 and n represents the integer 1, comprises reacting a teicoplanin-like compound with an excess of the suitable alcohol of formula ROH, wherein R is as previously defined but with the exclusion of the following meanings: ($C_1$–$C_3$)alkyl, β-polyhalogeno($C_1$–$C_{12}$)alkyl, phenyl, substituted phenyl,

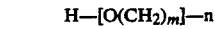
H—[O(CH$_2$)$_m$]—n wherein m is 2 or 3 and n represents the integer 1, in the presence of an acid catalyst such as 37% hydrochloric acid. Preferably, the alcohol of formula ROH is a liquid at the reaction temperature, so that it may act also as the reaction medium, without adding another suitable solvent. The reaction is preferably conducted under reduced pressure. The reaction temperature is generally between 50° and 80° C., when the reaction pressure is about 20 mmHg. When necessary, portions of a mixture of the 37% hydrochloric acid with the suitable alcohol are added from time to time to reintegrate the portions of reaction medium which evaporates. Portions of a suitable inert solvent capable of forming minimum azeotropic mixture with water are also added, and then the azeotrope which forms is distilled off under vacuum.

Representative examples of solvents capable of forming minimum azeotropic mixtures with water are benzene, toluene, butyl ether, carbon tetrachloride, chloroform, cyclohexane, 2,5-dimethylfurane, hexane, nonane, m-xilene and the like.

These alternate operations of addition of hydrochloric acid/alcohol mixture, minimum water azeotrope-forming inert solvent addition and of distillation of the aqueous azeotrope are repeated several times until the reaction is completed (i.e. the desired ester derivative is produced in acceptable or optimal yields).

Representative examples of ester derivatives of formula I which can be prepared according to these methods are: deglucoteicoplanin n-butyl ester, deglucoteicoplanin 1-methylpropyl ester, deglucoteicoplanin 1,1-dimethylethyl ester, deglucoteicoplanin pentyl ester, deglucoteicoplanin 1-methylbutyl ester, deglucoteicoplanin 2-methylbutyl ester, deglucoteicoplanin 1-hexanyl ester, deglucoteicoplanin 2-hexanyl ester, deglucoteicoplanin 3-hexanyl ester, deglucoteicoplanin 3,3-dimethyl-1-butanyl ester, deglucoteicoplanin 4-methyl-1-pentanyl ester; deglucoteicoplanin 3-methyl-1-pentanyl ester, deglucoteicoplanin 2,2-dimethyl-3-pentanyl ester, deglucoteicoplanin 2,4-dimethyl-3-pentanyl ester, deglucoteicoplanin 4,4-dimethyl-2-pentanyl ester, deglucoteicoplanin 5-methyl-2-hexanyl ester, deglucoteicoplanin 1-heptanyl ester, deglucoteicoplanin 2-heptanyl ester, deglucoteicoplanin 5-methyl-1-hexanyl ester, deglucoteicoplanin 2-ethyl-1-hexanyl ester, deglucoteicoplanin 2-methyl-3-hexanylester, deglucoteicoplanin 1-octanyl ester, deglucoteicoplanin 2-octanyl ester, deglucoteicoplanin 2-cyclopentylethanyl ester, deglucoteicoplanin 1-nonanyl ester, deglucoteicoplanin 2-nonanyl ester, deglucoteicoplanin 1-decanyl ester, deglucoteicoplanin 2-decanyl ester and deglucoteicoplanin 3-decanyl ester, deglucoteicoplanin 1-undecylester, deglucoteicoplanin 2-dodecyl ester, deglucoteicoplanin benzyl ester, deglucoteicoplanin m-chlorobenzyl ester, deglucoteicoplanin o-fluorobenzyl ester, deglucoteicoplanin m-fluorobenzyl ester, deglucoteicoplanin p-fluorobenzyl ester, deglucoteicoplanin m-methylbenzyl ester, deglucoteicoplanin m-methoxybenzyl ester, deglucoteicoplanin o-ethoxybenzyl ester, deglucoteicoplanin m-butoxybenzyl ester, deglucoteicoplanin p-tert.butoxybenzyl ester, deglucoteicoplanin p-tert.butylbenzyl ester, deglucoteicoplanin phenethyl ester, deglucoteicoplanin p-chlorophenethyl ester, deglucoteicoplanin m-chlorophenetyl ester, deglucoteicoplanin o-methoxyphenethyl ester, deglucoteicoplanin m-methoxyphenethyl ester, deglucoteicoplanin o-propylphenethyl ester, deglucoteicoplanin o-ethoxyphenethyl ester, deglucoteicoplanin p-fluorophenethyl ester, deglucoteicoplanin p-bromophenethyl ester, deglucoteicoplanin o-propoxyphenethyl ester, deglucoteicoplanin o-butoxyphenethyl ester, deglucoteicoplanin 1-(p-isopropylphenyl)ethyl ester, deglucoteicoplanin 3-phenyl-1-propyl ester, deglucoteicoplanin 2-phenyl-1-propyl ester, deglucoteicoplanin 4-phenyl-1-butyl ester and deglucoteicoplanin 3-phenyl-1-butyl ester, deglucoteicoplanin 2-chloroethyl ester, deglucoteicoplanin 2-bromoethyl ester, deglucoteicoplanin 3-chloropropyl ester, deglucoteicoplanin 3-fluoropropyl ester, deglucoteicoplanin 4-bromobutyl ester, deglucoteicoplanin 4-fluorobutyl ester, deglucoteicoplanin 5-iodopentyl ester, deglucoteicoplanin 2-bromo-2-methylpropyl ester, deglucoteicoplanin 3-chloro-2-methylpropyl ester, deglucoteicoplanin 4-chloro-3-methylbutyl ester, and the acid addition salts thereof.

A further general procedure for preparing the compounds of the invention, with the exception of those wherein R is a halogeno($C_1$–$C_{12}$)alkyl group, comprises reacting a N-protected deglucoteicoplanin, either in the non-salt form and in the presence of a hydrogen halide acceptor or in the form of the alkali metal (K, Na, Cs), silver, lead salt, with a halogenide derivative of formula RX, wherein R is as above with the exclusion of halogeno($C_1$–$C_{12}$)alkyl and X is chlorine or preferably bromine and iodine in an inert organic solvent. The reaction temperature is from about $-5°$ C. to $50°$ C. Preferably it is about $15°$–$20°$ C. The N-protected deglucoteicoplanin ester derivative is then N-deprotected according to the techniques outlined above or otherwise known in the art.

Examples of suitable inert organic solvents are polar aprotic solvents such as dimethylformamide, dimethoxyethane, hexamethylphosphoramide, dimethylsulfoxide, benzene, toluene and the like.

Examples of suitable hydrogen halide acceptors are tertiary organic amines such as triethylamine, picoline and the like as well as inorganic bases such as alkali metal bicarbonates, e.g. sodium or potassium bicarbonate.

Representative examples of the ester derivatives of formula I which can be prepared according to this method are: deglucoteicoplanin methyl ester, deglucoteicoplanin ethyl ester, deglucoteicoplanin propyl ester, deglucoteicoplanin 1-methylethyl ester, deglucoteicoplanin n-butyl ester, deglucoteicoplanin 1-methylpropyl ester, deglucoteicoplanin 1,1-dimethylethyl ester, deglucoteicoplanin pentyl ester, deglucoteicoplanin 1-methylbutyl ester, deglucoteicoplanin 2-methylbutyl ester, deglucoteicoplanin 1-hexanyl ester, deglucoteicoplanin 2-hexanyl ester, deglucoteicoplanin 3-hexanyl ester, deglucoteicoplanin 3,3-dimethyl-1-butanyl ester, deglucoteicoplanin 4-methyl-1-pentanyl ester; deglucoteicoplanin 3-methyl-1-pentanyl ester, deglucoteicoplanin 2,2-dimethyl-3-pentanyl ester, deglucoteicoplanin 2,4-dimethyl-3-pentanyl ester, deglucoteicoplanin 4,4-dimethyl-2-pentanyl ester, deglucoteicoplanin 5-methyl-2-hexanyl ester, deglucoteicoplanin 1-heptanyl ester, deglucoteicoplanin 2-heptanyl ester, deglucoteicoplanin 5-methyl-1-hexanyl ester, deglucoteicoplanin 2-ethyl-1-hexanyl ester, deglucoteicoplanin 2-methyl-3-hexanylester, deglucoteicoplanin 1-octanyl ester, deglucoteicoplanin 2-octanyl ester, deglucoteicoplanin 2-cyclopentylethanyl ester, deglucoteicoplanin 1-nonanyl ester, deglucoteicoplanin 2-nonanyl ester, deglucoteicoplanin 1-decanyl ester, deglucoteicoplanin 2-decanyl ester and deglucoteicoplanin 3-decanyl ester, deglucoteicoplanin 1-undecylester, deglucoteicoplanin 2-dodecyl ester, deglucoteicoplanin benzyl ester, deglucoteicoplanin m-chlorobenzyl ester, deglucoteicoplanin o-fluorobenzyl ester, deglucoteicoplanin m-fluorobenzyl ester, deglucoteicoplanin p-fluorobenzyl ester, deglucoteicoplanin m-methylbenzyl ester, deglucoteicoplanin m-methoxybenzyl ester, deglucoteicoplanin o-ethoxybenzyl ester, deglucoteicoplanin m-butoxybenzyl ester, deglucoteicoplanin p-tert.butoxybenzyl ester, deglucoteicoplanin p-tert.butylbenzyl ester, deglucoteicoplanin phenethyl ester, deglucoteicoplanin p-chlorophenethyl ester, deglucoteicoplanin m-chlorophenetyl ester, deglucoteicoplanin o-methoxyphenethyl ester, deglucoteicoplanin m-methoxyphenethyl ester, deglucoteicoplanin o-propylphenethyl ester, deglucoteicoplanin o-ethoxyphenethyl ester, deglucoteicoplanin p-fluorophenethyl ester, deglucoteicoplanin p-bromophenethyl ester, deglucoteicoplanin o-propoxyphenethyl ester, deglucoteicoplanin o-butoxyphenethyl ester, deglucoteicoplanin 1-(p-isopropylphenyl)ethyl ester, deglucoteicoplanin 3-phenyl-1-propyl ester, deglucoteicoplanin 2-phenyl-1-propyl ester, deglucoteicoplanin 4-phenyl-1-butyl ester, 1deglucoteicoplanin 3-phenyl-1-butyl ester, and the acid addition salts thereof.

Another procedure for preparing the compounds of the invention comprises reacting a carboxy activated N-protected deglucoteicoplanin derivative with a suitable alcohol in an inert organic solvent.

This procedure is particularly useful for preparing compounds of formula I wherein R is phenyl, substituted phenyl or $\beta$-(poly)halogenoalkyl, and in general sterically hindered groups which are prepared with difficulties or in very low yields by the above described processes.

According to this procedure, a N-protected deglucoteicoplanin ester is obtained which can be deprotected according to known per se techniques. Also the "activation" step of the N-protected deglucoteicoplanin derivative is obtained according to known per se techniques as described above and known in the art. Alternatively the N-protected deglucoteicoplanin derivative and the suitable alcohol are dissolved in an inert organic solvent and the condensing agent, dissolved in the same solvent, is added thereto. In any case, the reaction temperature is generally between −5° C. and room temperature, preferably between 0° and 15°–20° C. Inert organic solvents are polar aprotic solvents as above defined while suitable condensing agents are as above described when dealing with the "activation" of the carboxy function of the deglucoteicoplanin nucleus. Representative examples of the ester derivatives of formula I which can be prepared according to this method are: deglucoteicoplanin phenyl ester, deglucoteicoplanin 4-chlorophenyl ester, deglucoteicoplanin 4-bromophenyl ester, deglucoteicoplanin 4-fluorophenyl ester, deglucoteicoplanin 3,4-dibromophenyl ester, deglucoteicoplanin 3,4-difluorophenyl ester, deglucoteicoplanin 3,4-dichlorophenyl ester, deglucoteicoplanin 3-bromo-4-chlorophenyl ester, deglucoteicoplanin 2,4-dichlorophenyl ester, deglucoteicoplanin 2,4-dibromophenyl ester, deglucoteicoplanin 2,4-difluorophenyl ester, deglucoteicoplanin 2,4,6-tribromophenyl ester, deglucoteicoplanin 2,4,6-trichlorophenyl ester, deglucoteicoplanin 4-methyl-2-chlorophenyl ester, deglucoteicoplanin 4-methyl-2-bromophenyl ester, deglucoteicoplanin 4-methoxy-2-chlorophenyl ester, deglucoteicoplanin 1-bromoethyl ester, deglucoteicoplanin 1,1-dichloroethyl ester, deglucoteicoplanin 1-fluoroethyl ester, deglucoteicoplanin 1,1-difluoroethyl ester, deglucoteicoplanin 1-bromo-2-chloroethyl ester, deglucoteicoplanin 1,1-dichloropropyl ester, deglucoteicoplanin 1-chloro-1-methylethyl ester, deglucoteicoplanin 1,1-dichloro-2-methylpropyl ester, deglucoteicoplanin 1-bromo-2-methylpropyl ester, deglucoteicoplanin 1,1,1-trifluoromethyl ester, deglucoteicoplanin 1-chloromethyl ester; the N-protected intermediates to such compounds and the acid addition salts thereof. The compounds of formula I wherein R is

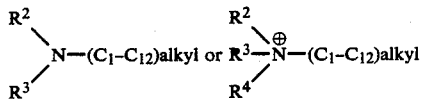

wherein $R^2$, $R^3$ and $R^4$ are as above defined, are preferably prepared by reacting the corresponding free-amino (or N-protected) chloro-, bromo- or iodo-$(C_1-C_{12})$alkyl deglucoteicoplanin ester with the proper amine of formula

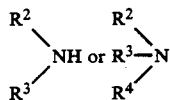

in an inert organic solvent such as dimethylformamide, dimethoxyethane, dimethylsulfoxide, benzene, toluene and the like, or in the presence of an excess of the amine as the reaction solvent, at a temperature between −5° C. and room temperature. Preferably the reaction temperature is between +5° C. and 20° C.

It will be recognized by those skilled in the art that the reaction time in the above reported esterification procedures varies depending on the specific reaction conditions and on the starting materials which are employed; however since the compounds of the invention as well as the teicoplanin-like starting materials can be easily detected by TLC or HPLC methods, the skilled technician is also capable of monitoring the reaction course and determining when it is completed.

An example of the way in which the reaction course may be monitored by HPLC is as follows: of about 20 μl are drawn from the reaction mixture at predetermined times, diluted to a final concentration of about 2 mg/ml in a mixture 0.2% aqueous ammonium formate/acetonitrile, 50:50 (v/v) and injected into the HPLC system.

The HPLC system is a chromatograph Varian 5000 equipped with 20 μl loop injector Rheodyne 7125; a UV detector at 254 nm and pre-column packed with Perisorb RP-8 Merck (30–40 μm) followed by a Hibar Merck column (25 cm) pre-packed with LiChrosorb RP-8 (10 μm). Eluents: linear gradient from 5% B in A to 60% B in A in 30 min, at a flow rate of about 3 ml/min;

solution A: 0.2% aqueous ammonium formate;
solution B: acetonitrile.

The relative retention times of some representative compounds of the invention in the above system are reported in Table I below. The values marked with an asterisk are obtained according to the above procedure but using the following elution system:

solution. A: 0.02 M solution NaH in water
solution B: acetonitrile
gradient: B% in A t 0–%B 15, t 10–%B 30, t 20–%B 60, t 25–%B 80, t 30–%B 15
flow rate: 2.0 ml/min It will be appreciated by those skilled in the art that the compounds of the invention can be prepared either from an essentially pure teicoplanin-like substance or from a crude teicoplanin-like substance.

In the former case, a compound of the invention can be obtained which may not need further purification, while in the latter case a final purification step is necessary. However, when a further purification is necessary or desirable it can be done according to usual purification techniques and, in particular, by column chromatography.

A preferred purification procedure involves the use of a reverse phase column chromatography. A preferred adsorbent in this case is the silanized silica gel having a distribution particle range of 0.06–0.2 mm. The eluent can be one of the hydrophilic mixtures that can be used in this purification technique. Representative examples of these hydrophilic eluents are the mixtures of diluted aqueous solution of ammonium salts of organic acids, acetonitrile or water soluble lower alkanols.

Representative examples of diluted aqueous solutions of ammonium salts of organic acids are 0.1–6% ammonium formate aqueous solutions, while examples of suitable alkanols are methanol, ethanol, propanol and the like. Preferred eluents are a mixture of aqueous ammonium formate and acetonitrile at a pH between 6 and 8 or a mixture of aqueous ammonium formate and methanol. A preferred procedure includes a first reverse phase chromatography on silanized silica gel (0.06–0.2 mm) developing with a linear step-gradient of 5 to 60% acetonitrile in 0.2% aqueous ammonium formate and a second column chromatography which uses a mixture of acetonitrile/water, 6:4 (v/v), as the eluent.

Another preferred procedure includes:
(a) contacting a solution of the crude antibiotic in 0.2% aqueous ammonium formate/methanol/butanol, 1:2:3, with silanized silica gel and stripping off the solvents,
(b) applying the residue at the top of a silanized silica gel (0.06–0.2 mm) column, developing with 0.6% aqueous ammonium formate and acetonitrile, 9:1, discarding the eluate and continuing the elution with a linear gradient of acetonitrile in water, obtained by mixing acetonitrile/water 1:9 and acetonitrile/water 7:3 at a rate of 200 ml/h.

The term "essentially pure" as referred to an antibiotic substance of the present disclosure, refers to substances having an HPLC titre greater than 95% (percent peak areas, at the pre-determined—254 nm—UV wavelength), a water and solvents content from 10% to 15% (by weight) and an inorganic residue lower than 0.5% (by weight).

The physico-chemical characteristics of representative compounds of the invention (the compounds of formula I wherein A, B, and Z represent independently hydrogen groups and R and $R^1$ are as indicated in Table I below) are summarized in the following Tables I, II, III:

TABLE I

| Example No. | R | $R^1$ | IR($\lambda$max, cm$^{-1}$)[a] ($\nu$C=O ester) | K[b] | pK$_a$[c] |
|---|---|---|---|---|---|
| 1 | n-butyl | H | 1720 | 1.63 | 6.57 |
| 2 | n-octyl | H | 1715 | 2.17 | 6.82 |
| 3 | benzyl | H | 1730 | 1.69 | 6.67 |
| 4 | H | benzyloxycarbonyl | — | 2.01 | 5.02 |
| 5 | pivaloyloxymethyl | benzyloxycarbonyl | | | |
| 6 | pivaloyloxymethyl | H | 1740 | | 6.52 |
| 7 | ethyl | benzyloxycarbonyl | | | |
| 8 | ethyl | H | | | |
| 9 | 4-clorobutyl | H | 1725 | 1.72 | 6.60 |
| 10 | H | t.butoxycarbonyl | ~1730 | 1.44* | |
| 11 | methyl | t.butoxycarbonyl | | | |
| 12 | methyl | H | | 1.25 | |
| 13 | 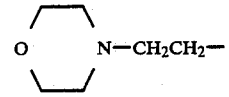 | t.butyloxycarbonyl | | | |
| 14 | 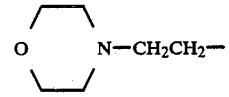 | H | | 1.64 | 5.3 and 7.5 |
| 15 | HOCH$_2$CH$_2$— | t.butoxycarbonyl | | | |
| 16 | HOCH$_2$CH$_2$— | H | | 1.18 | |
| 17 | Br—CH$_2$CH$_2$— | benzyloxycarbonyl | 1730 | | |
| 18 | Br—CH$_2$CH$_2$— | H | 1740 | | |
| 19 | F—CH$_2$CH$_2$— | benzyloxycarbonyl | | | |
| 20 | F—CH$_2$—CH$_2$— | H | 1735 | | |

Notes to Table I:
[a] registered in a nujol mull with a Perkin-Elmer 850 instrument

[b] $K = \dfrac{t_R \text{ ester}}{t_R \text{ deglucoteicoplanin}}$ = relative retention time in the HPLC system described above $t_R$ deglucoteicoplanin in this system ≈ 11.4 min.

[c] the samples are dissolved in methylcellosolve ®/water 4:1 (v/v), an excess of 0.01 M hydrogen chloride in the same mixture is added thereto and the resulting solution is titrated with 0.01 M NaOH in the same solvent mixture

TABLE II

| | UV ($\lambda$ max) (nm)* | | | |
|---|---|---|---|---|
| Example No. | Methanol | pH = 1.0 | pH = 7.4 | pH = 13.0 |
| 1 | 280 | 279 | 279 | 298 |
| 2 | 280 | 279 | 279 | 298 |
| 3 | 280 | 279 | 278 | 297 |
| 4 | 280 | N.D.[a] | 280 | 297 |
| 6 | 280 | N.D. | N.D. | N.D. |
| 9 | 280 | 279 | 278 | 298 |

*recorded by means of a Unicam SP 800 spectrometer
[a] N.D. means "not done"

TABLE III

ELEMENTAL ANALYSIS

| Example No. | Calcd. formula (MW) | C %[a] calcd. | C %[a] found | H %[a] calcd. | H %[a] found | N %[a] calcd. | N %[a] found | Cl % (total)[b] calcd. | Cl % (total)[b] found | Cl % (ionic)[b] calcd. | Cl % (ionic)[b] found |
|---|---|---|---|---|---|---|---|---|---|---|---|
| 1 | C$_{62}$H$_{53}$N$_7$Cl$_2$O$_{18}$.HCl (1291.54) | 57.66 | 57.28 | 4.21 | 4.40 | 7.59 | 7.34 | 8.24 | 8.75 | 2.75 | 3.30 |
| 2 | C$_{66}$H$_{61}$N$_7$Cl$_2$O$_{18}$.HCl (1347.64) | 58.82 | 58.68 | 4.64 | 5.13 | 7.28 | 7.07 | 7.89 | 8.55 | 2.63 | 3.13 |
| 3 | C$_{65}$H$_{51}$N$_7$Cl$_2$O$_{18}$.HCl (1325.55) | 58.90 | 58.57 | 3.95 | 4.14 | 7.40 | 7.28 | 8.02 | 7.90 | 2.67 | 2.66 |
| 4 | C$_{66}$H$_{51}$N$_7$Cl$_2$O$_{20}$ (1333.10) | 59.46 | 59.75 | 3.86 | 4.33 | 7.36 | 6.97 | 5.32 | 5.23 | — | |
| 5 | C$_{72}$H$_{61}$N$_7$Cl$_2$O$_{22}$ (1447.25) | 59.75 | 59.89 | 4.25 | 4.60 | 6.78 | 6.82 | 4.90 | 5.20 | — | |
| 6 | C$_{64}$H$_{55}$N$_7$Cl$_2$O$_{20}$.HCl | 56.95 | 56.22 | 4.18 | 4.31 | 7.26 | 7.36 | 7.88 | 7.48 | 2.62 | 3.02 |
| 7 | C$_{68}$H$_{55}$N$_7$Cl$_2$O$_{20}$ | 60.00 | 59.20 | 4.07 | 4.40 | 7.20 | 7.10 | 5.20 | 5.75 | — | |

TABLE III-continued
ELEMENTAL ANALYSIS

| | | | | | | | | | | |
|---|---|---|---|---|---|---|---|---|---|---|
| | (1361.13) | | | | | | | | | |
| 9 | $C_{62}H_{52}N_7Cl_3O_{18}$ | 57.75 | 57.02 | 4.06 | 4.17 | 7.60 | 7.42 | 8.25 | 8.22 | — |
| | (1289.5) | | | | | | | | | |
| 10 | $C_{63}H_{53}Cl_2N_7O_{20}$ | 58.25 | 57.95 | 4.11 | 4.80 | 7.54 | 7.93 | | | |
| | (1299) | | | | | | | | | |
| 17 | $C_{68}H_{54}N_7BrCl_2O_{20}{}^{(e)}$ | 56.71 | 56.59 | 3.78 | 4.15 | 6.80 | 6.65 | 4.92 | 4.55 | |
| | (1440) | | | | | | | | | |
| 0 | $C_{60}H_{48}N_7FCl_2O_{18}{}^{(f)}$ | 56.24 | 56.35 | 3.85 | 4.20 | 7.65 | 7.32 | | | |
| | .HCl | | | | | | | | | |
| | (1281.5) | | | | | | | | | |

| Example No. | Calcd. formula (MW) | inorganic[c] residue % | weight[d] loss % |
|---|---|---|---|
| 1 | $C_{62}H_{53}N_7Cl_2O_{18}$ .HCl (1291.54) | 0.1 | 9.5 |
| 2 | $C_{66}H_{61}N_7Cl_2O_{18}$ .HCl (1347.64) | 0.2 | 10.6 |
| 3 | $C_{65}H_{51}N_7Cl_2O_{18}$ .HCl (1325.55) | 0.2 | 10.1 |
| 4 | $C_{66}H_{51}N_7Cl_2O_{20}$ (1333.10) | 0.15 | 10.3 |
| 5 | $C_{72}H_{61}N_7Cl_2O_{22}$ (1447.25) | 0.20 | 10.5 |
| 6 | $C_{64}H_{55}N_7Cl_2O_{20}$ .HCl | 0.15 | 9.5 |
| 7 | $C_{68}H_{55}N_7Cl_2O_{20}$ (1361.13) | 0.4 | 10.5 |
| 9 | $C_{62}H_{52}N_7Cl_3O_{18}$ (1289.5) | 0.3 | 8.4 |
| 10 | $C_{63}H_{53}Cl_2N_7O_{20}$ (1299) | | |
| 17 | $C_{68}H_{54}N_7BrCl_2O_{20}{}^{(e)}$ (1440) | 0.1 | 6.7 |
| 0 | $C_{60}H_{48}N_7FCl_2O_{18}{}^{(f)}$ .HCl (1281.5) | 0.3 | 6.7 |

[a] Determined on samples previously dried at 140° C. under nitrogen atmosphere
[b] Corrected for weight loss and inorganic residue
[c] Determined after heating the samples at 900° C. in oxygen atmosphere
[d] Determined by thermogravimetric analysis at 140° C.
[e] Determined on samples previously dried at 140° C. under nitrogen atmosphere: Br % Calcd. 5.54; Found 5.13
[f] Determined on samples previously dried at 140° C. under nitrogen atmosphere: F % Calcd. 1.48; Found 1.53

The antibacterial activity of the compounds of the invention can be demonstrated in vitro by means of standard agar-dilution tests.

Isosensitest broth (Oxoid) and Todd-Hewitt broth (Difco) are used for growing staphylococci and streptococci, respectively. Broth cultures are diluted so that the final inoculum is about $10^4$ colony forming units/ml (CFU/ml). Minimal inhibitory concentration (MIC) is considered as the lowest concentration which shows no visible growth after 18–24 h incubation at 37° C. The results of the antibacterial testing of representative compounds of formula I are summarized in table IV below:

TABLE IV

| | MIC (μg/ml) of the compounds of Example No. | | |
|---|---|---|---|
| MICROORGANISM | 1 | 2 | 3 |
| S. aureus ATCC 6538 | 0.05 | 0.2 | 0.4 |
| S. aureus TOUR ($10^3$ CFU/ml) | 0.1 | 0.2 | 0.4 |
| S. aureus TOUR ($10^6$ CFU/ml) | 0.4 | 0.8 | 0.4 |
| S. aureus TOUR + 30% bovine serum | 0.4 | 0.8 | 0.8 |
| S. epidermidis ATCC 12228 | 0.05 | 0.1 | 0.1 |
| S. pyogenes C 203 SKF 13400 | 0.1 | 0.05 | 0.05 |
| S. pneumoniae UC 41 | 0.1 | 0.05 | 0.2 |
| S. faecalis ATCC 7080 | 0.2 | 0.4 | 0.4 |
| E. coli SKF 12140 | 50 | >100 | 12.5 |

In addition to the antimicrobial activity against gram-positive bacteria, representative compounds of the invention possess a certain degree of activity against gram-negative bacteria.

In view of the above the compounds of the present invention can effectively be employed as the active ingredient of antimicrobial preparations used in human and veterinary medicine for the prevention and treatment of infectious diseases caused by pathogenic bacteria which are susceptible to said active ingredients. In such treatments, these compounds may be employed as such or also in the form of mixtures in any proportion. The compounds of the present invention can be administered orally, topically or parenterally wherein however, the parenteral administration is preferred. Depending on the route of administration, these compounds can be formulated into various dosage forms. Preparations for oral administration may be in the form of capsules, tablets, liquid solutions or suspension. As known in the art the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents. For topical use the compounds of the present invention may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-liquid form. Topical applications may be formulated in hydrophobic or hydrophilic bases as ointments, creams, lotions, paints, or powders.

Compositions for injection may take such forms as suspensions, solutions, or emulsions in oily or aqueous vehicles, and may contain formulatory agents such as suspending, stabilizing and/or dispersing agents. Alternatively, the active ingredient may be in powder form for reconstitution at the time of delivery with a suitable vehicle, such as sterile water.

The amount of active principle to be administered depends on various factors such as the size and condition of the subject to be treated, the route and frequency of administration, and the causative agent involved.

The compounds of the invention are generally effective at a daily dosage comprised between about 0.5 and about 30 mg of active ingredient per Kg of body weight, preferably divided in 2 to 4 administrations per day. Particularly desirable compositions are those prepared in the form of dosage units containing from about 20 to about 300 mg per unit.

Representative examples of preparation of pharmaceutical compositions are as follows:

A parenteral solution is prepared with
 100 mg of deglucoteicoplanin benzyl ester, hydrochloride dissolved in 2 ml of sterile water for injection A parenteral solution is prepared with
 250 mg of deglucoteicoplanin n-butyl ester, hydrochloride dissolved in 3 ml of sterile water for injection A topical ointment is prepared with
 200 mg of deglucoteicoplanin n-octyl ester, hydrochloride
 3.6 g of polyethylene glycol 4000 U.S.P.
 6.2 g of polyethylene glycol 400 U.S.P.

Besides their activity as medicaments, the compounds of the present invention can be used as animal growth promoters.

For this purpose, one or more of the compounds of the invention is administered orally in a suitable feed. The exact concentration employed is that which is required to provide for the active agent in a growth promotant effective amount when normal amounts of feed are consumed.

The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and Co., S. Francisco, USA, 1969 or "Livestock Feeds and Feeding", 0 and B Books, Corvallis, Oregon, USA, 1977) and are incorporated herein by reference.

Physico-chemical characteristics of antibiotic L 17054

Antibiotic L 17054 has the following characteristics (a) the specific rotation $[\alpha]_D^{20}$ is $-34°$ (c=1%, DMF)

(b) it is freely soluble in water at pH>8.0, in dimethylformamide, dimethylsulfoxide, propyleneglycol and methylcellosolve; slightly soluble in methanol; almost insoluble in ethyl ether and acetone.

(c) an ultraviolet absorption spectrum which has the following absorption maxima:
 in 0.1 N hydrochloric acid: $\lambda_{max}$278 nm ($E_{1cm}^{1\%}$=60.6)
 in 0.1 N sodium hydroxide: $\lambda_{max}$297 nm ($E_{1cm}^{1\%}$=118.8)
 in phosphate buffer pH 7.4: $\lambda_{max}$277 nm ($D_{1cm}^{1\%}$=70.3)

(d) an infrared absorption spectrum in nujol with the following absorption maxima (cm$^{-1}$): 3700-2000, 2970-2850 (nujol), 1655, 1610, 1595, 1515, 1490, 1460 (nujol), 1375 (nujol), 1300, 1230, 1145, 1060, 1020, 970, 890, 850, 820, 720 (nujol)

(e) an elemental analysis, after the sample has been previously dried at about 140° C. under inert atmosphere (weight loss=7.8%), which indicated the following approximate percentage composition (average): carbon 55.46%; hydrogen, 4.50%; nitrogen 7.20%; chlorine 4.67%; ashes 0.2%

(f) it has the following $R_f$ values in the TLC systems indicated below:

| Elution system (v/v) | $R_f$ value |
| --- | --- |
| (I) Acetonitrile/water 75:25 (silica gel Merck 60 F$_{254}$) | 0.32 |
| (II) Acetonitrile/5% aqueous sodium sulfate 30:70 (silica gel Merck silanized 60 F$_{254}$) | 0.61 |

Visualization: UV-light at 254 nm; 3% ethanolic ninhydrine; 1% methanolic fluorescamine;

(g) a retention time ($t_R$) of 8.3 minutes when analyzed by HPLC using a 150×4.0 mm Zorbax ®ODS (5-6 μm) column (Zorbax is a trademark of the Dupont Co. for an octadecylsilane silica gel matrix), and eluting with a linear gradient from 0% to 50% solution B in solution A in 40 minutes (solution A: 25 mM aqueous NaH$_2$PO$_4$/acetonitrile (9:1) buffered at pH 6.0 with 0.1 N NaOH; solution B: 25 mM NaH$_2$PO$_4$/acetonitrile (3:7) buffered at pH 6.0 with 0.1 N NaOH), with a flow rate of 2 ml/min.; (internal standard: 3,5-dihydroxytoluene $t_R$ 5.60 minutes)

(h) the $^1$H NMR spectrum is registered at 270 MHz with a Bruker WH-270 Spectrometer, in DMSO-d$_6$ at 60° C. and with a sample concentration of 20 mg/ml (internal standard TMS, $\delta$=0.00 ppm).

Some of the $^1$H NMR data obtained after D$_2$O exchange and selective decoupling experiments are as follows ($\delta$ppm, multiplicity): 1.88, s; 2.85, d; ~3.5, dd; 3-4; 4.20, d; 4.48, d; 4.50, d; 4.62, s; 4.96, ddd; 5.18 d; 5.31, s; 5.35, d; 5.39, s; 5.68, d; 5.71, s; 6.20, d; 6.41, s; 6.51, s; 6.56, s; 6.74, d; 6.77, s; 6.80, s; 6.80, d; 6.98, d; 7.08, s; 7.15, d; 7.21, d; 7.28, d; 7.35, d; 7.50, d; 7.56, d; 7.64, d; 7.73, d; 7.86, s; 8.42, d.

(i) a potentiometric titration profile which shows three titration slopes with pH½ values equal to 5.0 (one equivalent), 7.0 (one equivalent), and 11 (five equivalents) in methylcellosolve/water 4:1 upon titrating a solution of the test compound containing an excess of 0.01 N HCl in methylcellosolve/water 4:1 with 0.01 N NaOH in the same solvent mixture (l) an acidic function capable of forming salts
(m) a basic function capable of forming salts
(n) two sugar residues which are α-D-mannosyl and N-acetyl-β-D-glucosaminyl.

Physico-chemical characteristics of antibiotic L 17046

Antibiotic L 17046 has the following characteristics (a) the specific rotation $[\alpha]_D^{20}$ is $-44°$(c=1%, DMF)
(b) it is freely soluble in water at pH>8.0, in dimethylformamide, dimethylsulfoxide, propyleneglycol and methylcellosolve; slightly soluble in methanol; almost insoluble in n.hexane, ethyl ether and acetone.
(c) it has an ultraviolet absorption spectrum that exhibits the following absorption maxima:
in 0.1 N hydrochloric acid: $\lambda_{max}278$ nm $(E_{1cm}^{1\%}=67.1)$
in 0.1 N sodium hydroxide: $\lambda_{max}297$ nm $(E_{1cm}^{1\%}=124.1)$
in phosphate buffer pH 7.4: $\lambda_{max}277$ nm $(E_{1cm}^{1\%}=75.0)$
(d) an infrared absorption spectrum in nujol with the following observable absorption maxima (cm$^{-1}$): 3700-2000, 2970-2850 (nujol), 1655, 1610, 1595, 1515, 1490, 1460 (nujol), 1375 (nujol), 1300, 1230, 1145, 1060, 1010, 890, 850, 820, 720 (nujol)
(e) an elemental analysis, after the sample has been previously dried at about 140° C. under inert atmosphere (weight loss=8.4%), which indicates the following approximate percentage composition (average): carbon 56.74%; hydrogen, 4.27%; nitrogen, 7.99%; chlorine, 5.11%; ashes, 0.6%
(f) the following $R_f$ values in the TLC systems indicated below:

| Elution system (v/v) | $R_f$ value |
|---|---|
| (I) Acetonitrile/water 75:25 (silica gel Merck 60 F$_{254}$) | 0.53 |
| (II) Acetonitrile/5% aqueous sodium sulfate 30:70 (silica gel Merck silanized 60 F$_{254}$) Visualization: UV-light at 254 nm; 3% ethanolic ninhydrine; 1% methanolic fluorescamine; | 0.54 |

(g) a retention time ($t_R$) of 10.8 minutes when analyzed by reversed phase HPLC using a 150×4.0 mm Zorbax®ODS (5-6 μm) column (Zorbax is a trademark of the Dupont Co. for a octadecylsilane silica matrix), and eluting with a linear gradient from 0% to 50% solution B in solution A in 40 minutes solution A: 25 mM NaH$_2$PO$_4$/acetonitrile (9:1) buffered at pH 6.0 with 0.1 N NaOH solution B: 25 mM NaH$_2$PO$_4$/acetonitrile (3:7) buffered at pH 6.0 with 0.1 N NaOH), with a flow rate of 2 ml/min.; (internal standard: 3,5-dihydroxytoluene $t_R$ 5.60 minutes)

(h) the $^1$H NMR spectrum registered at 270 MHz with a Bruker WH-270 Spectrometer, in DMSO-d$_6$ at 60° C. and with a sample concentration of 20 mg/ml (internal standard TMS, δ=0.00 ppm).

Some of the $^1$H NMR data obtained after D$_2$O exchange and selective decoupling experiments are as follows (δppm, multiplicity):

1.86, s; 2.81, d; 3.5, dd; ~3-4; 4.12, d; 4.32, d; 4.37, d; 4.56, s; 4.95, ddd; 5.07, s; 5.31, d; 5.39, s; 5.51, s; 5.66, d; 6.12, s; 6.29, s; 6.32, s; 6.37, s; 6.42, s; 6.60, d; 6.62, s; 6.64, s; 6.92, d; 7.09, s; 7.12, d; 7.21, d; 7.25, d; 7.43, d; 7.64, d; 7.66, d; 7.70, d; 7.85, s; 8.12, d; 8.46, d; ~9.5, s.

(i) a potentiometric titration profile which shows three titration slopes with pH½ values equal to 5.0 (one equivalent), 7.0 (one equivalent), and 11 (five equivalents) in methylcellosolve/water 4:1 upon titrating a solution of the test compound containing an excess of 0.01 N HCl in methylcellosolve/water 4:1 with 0.01 N NaOH in the same solvent mixture (l) an acidic function capable of forming salts
(m) a basic function capable of forming salt
(n) a sugar residue which is N-acetyl-β-D-glucosaminyl.

Physico-chemical characteristics of antibiotic L 17392

Antibiotic L 17392 has the following characteristics (a) it is soluble in water at a pH higher than 9 and aqueous methanol, ethanol and acetone; slightly soluble in ethyl alcohol and dimethylformamide (b) an ultraviolet absorption maxima which shows the following absorption maxima
in 0.1 N hydrochloric acid: $\lambda_{max}279$ nm $(E_{1cm}^{1\%}=82.9)$
in 0.1 N sodium hydroxide: $\lambda_{max}297$ nm $(E_{1cm}^{1\%}=155.6)$ (c) an infrared absorption spectrum in nujol with the following mainly significant absorption maxima (cm$^{-1}$):

3250 (νNH and phenolic νOH)
1645 (Amide I)
1610 (νCOO$^-$)
1595 (δNH$_3^+$)
1520 (Amide II)

(d) the $^1$H NMR spectrum registered at 270 MHz with a Bruker WH-270 Spectrometer, in DMSO-d$_6$ at 50° C. (internal standard TMS, δ=0.00 ppm).

Some of the $^1$H NMR data obtained after D$_2$O exchange and selective decoupling experiments are as follows (δppm, multiplicity): 2.85-3.30, 2dd; 4.12, dd; 4.37, d; 4.45, d; 4.50, s; 5.00, ddd; 5.11, d; 5.14, d; 5.35, d; 5.56, d; 5.60, d; 6.3-7.9, m; 6.55, d; 7.37, d; 7.50, d; 7.61, d; 8.26, d; 8.28, d; 8.5-10.2, br;

d = doublet.
dd = doublets of doublets
ddd = doublet of doublets of doublets
s = singlet
m = multiplet
br = broad (e) an elemental analysis which indicates the following approximate percentage composition (average): carbon 58.27%; hydrogen 3.73%; nitrogen 7.86%; chlorine 6.04%; (after correction for weight loss—measured by thermal gravimetric analysis—and for inorganic residue, determined after having heated the samples to 900° C. in oxygen atmosphere).

(f) a molecular weight of 1199 confirmed also by FAB-MS analysis.

(g) formula [calculated on the basis of the available data]:

$C_{58}H_{45}Cl_2N_7O_{18}$.

(h) a retention time ($t_R$) of 12.2 min when analyzed by HPLC using a pre-column (5 cm) packed with Perisorb RP8 (30 μm Merck) followed by a column Hibar RT250-4 (Merck) prepacked with LiChrosorb RP8 (10 μm) and eluting with a liner step-gradient ranging from 10% to 30% acetonitrile in 0.2% aqueous ammonium formate; flow rate: 2 ml/min (internal standard: Teicoplanin A₂ component 2 of British Patent Application Publication No. 2121401, $t_R$=22.4 min)

(j) an acidic function capable of forming salts.
(l) a basic function capable of forming salts
(m) no sugar residue.

The following examples illustrate the manner in which the invention can be practiced, but, as such, should not be construed as limiting its overall scope.

Preparation of the starting materials (a) Preparation of antibiotic L 17054

5 g of teicoplanin is added to 60 ml of 0.5 N aqueous hydrochloric acid pre-heated to 80° C. with vigorous stirring.

Stirring is continued and the temperature is maintained at about 80° C. for 30 minutes. Then, the mixture is rapidly filtered, the filtrate is cooled to 0–5° C. and 6 N hydrochloric acid (10 ml) is added. The resulting suspension is stirred for about 15 minutes while keeping the temperature at 0°–5° C. The precipitate is collected, washed with 20 ml of cold 1 N HCl and then with ethyl ether, and dried under reduced pressure at room temperature resulting in crude antibiotic L 17054 hydrochloride (4.5 g).

Crude antibiotic L 17054 hydrochloride (3 g) as obtained above is suspended in a mixture of 0.2% aqueous HCOONH₄/CH₃CN 95:5 (v/v) (150 ml). The pH is brought to about pH 7.5 with 1 N NaOH and the product is dissolved. The resulting solution is applied to a column containing 150 g of 0.06–0.2 mm silanized silica gel Merck prepared in the same solvent mixture. The column is developed with a linear gradient elution, from 5 to 21% of acetonitrile in 0.2% aqueous ammonium formate (v/v), collecting 20 ml fractions, which are monitored by HPLC. L 17054 containing fractions (70 to 96) are combined and the acetonitrile is removed under vacuum. The residual aqueous solution is applied to a column of 10 g of silanized silica gel in distilled water. After washing with distilled water until the salts are completely eliminated the product is eluted with a 1:1 (v/v) CH₃CN:H₂O mixture. The collected solution is concentrated under vacuum to a small volume and the antibiotic is precipitated by adding acetone. After drying at room temperature, 0.9 g of essentially pure antibiotic L 17054 is obtained.

Preparation of antibiotic L 17046

Teicoplanin (10 g) is added to 1 N hydrochloric acid (150 ml) preheated to 80° C. while stirring.

After about 45 minutes the reaction mixture is cooled to 0°–5° C. and 37% hydrochloric acid (~30 ml) is added. Stirring is maintained for about 10 minutes, after which the precipitated solid is recovered by filtration, washed with 20 ml of 2 N HCl, then with ethyl ether, and dried overnight over potassium hydroxide pellets at room temperature, resulting in crude antibiotic L 17046 hydrochloride (8.3 g).

The above crude product (6.2 g) is dissolved in 80% methanol (500 ml) and silica gel (30 g; Merck 0.06–0.2 mm) is added. After the addition of n-butanol (200 ml) the solvent is removed under vacuum. The residue is then applied to a silica gel chromatography column (300 g) in acetonitrile. The column is developed by using sequentially 300 ml each of the following solvent mixtures: acetonitrile, acetonitrile:water 95:5, acetonitrile:water, 90:10; acetonitrile:water, 85:15. The eluates are discarded and the column is developed with a linear gradient eluent obtained by mixing 3.5 l each of the following mixtures: acetonitrile:water, 83:17 and acetonitrile:water, 70:30 at a rate of 375 ml/h.

Fractions of 25 ml each are collected and monitored by HPLC. The fractions which contain antibiotic L 17046 (fractions 170 to 200) are combined. n-Butanol (400 ml) is added to the pooled fractions and the resulting mixture is concentrated to a small volume. Acetone is then added to the cloudy solution and, after cooling to 10° C. a precipitate begins to form. After suitable time, the precipitation is complete and the solid is then collected by filtration, washed with acetone, then with ether, dried under vacuum at room temperature, yielding the compound of the title in essentially pure form (1.9 g).

(c) Preparation of deglucoteicoplanin

Teicoplanin (10 g) is dissolved in 90% aqueous trifluoroacetic acid (250 ml) and heated to about 80° C. for about 2 hours. After cooling to room temperature, the reaction mixture is poured into ice-cooled ethyl ether (1 liter). The obtained precipitate is collected by filtration, washed with ethyl ether and dried in the air to obtain the crude trifluoroacetic acid addition salt of antibiotic deglucoteicoplanin (6.3 g).

5.3 g of this crude material are dissolved in 1 liter of a mixture of 0.2% ammonium formate/methanol/n-butanol, 1:2:3 and silanized silica gel 60 Merck (0.06–0.2 mm) (20 g) is added thereto. After appropriate stirring, the solvents are stripped off under vacuum and the residue is applied to the top of a chromatographic column prepared with 750 g of silanized silica gel (0.06–0.2 mm; Merck) in water. The column is developed with a mixture of 0.6% aqueous HCOONH₄ and CH₃CN, 9:1. The eluate is discarded, then the elution is continued with a linear gradient of acetonitrile in water from 1:9 to 3:7 at a rate of 200 ml/h for about 30 h. Fractions of 25 ml each are collected and monitored by HPLC. The deglucoteicoplanin containing fractions (200 to 250) are pooled and n-butanol is added. After stirring the mixture is concentrated to a small volume, ethyl ether is added and the solid which separates is collected by filtration, washed with ethyl ether and dried at 40° C. under vacuum, yielding 0.9 g of essentially pure antibiotic deglucoteicoplanin.

(d) Preparation of Teicoplanin

Teicoplanin is prepared by cultivating the strain *Actinoplanes teichomyceticus* ATCC 31121 as disclosed in U.S. Pat. No. 4,239,751 and purified by means of Sephadex ® column chromatography or other equivalent purification technique.

EXAMPLE 1

Preparation of antibiotic deglucoteicoplanin n-butyl ester, hydrochloride (a) from antibiotic L 17046

To a stirred suspension of 1.75 g of antibiotic L 17046 in 56 ml of n-butanol, 4.5 ml of butanolic 6.5 M hydrogen chloride is added at room temperature. The reaction mixture is heated to 60–65° C. and stirred for 12 h. The clear solution which forms is kept at room temperature overnight, then concentrated under vacuum to a small volume (~30 ml). Water (200 ml) is added and the resulting mixture is extracted with ethyl acetate (200 ml). The organic layer is separated, butanolic 1 M hydrogen chloride (1.2 ml) is added and the solution is concentrated to a small volume (~20 ml) under vacuum. By adding a mixture of ether/acetone 3:1 (v/v) a solid separates which is collected, washed with ether and dried at 40° C. under vacuum for 8 h yielding 0.93 g of antibiotic deglucoteicoplanin n-butyl ester, hydrochloride.

Essentially following the procedure of the foregoing Example 1 but substituting teicoplanin, teicoplanin $A_2$ component 2, antibiotic L 17054 or any mixture thereof for antibiotic L 17046 as the starting material, the same compound of the title is obtained in similar yields (from 0.80 to 1.1 g, employing the same molar amount of reactant as in the foregoing Example).

EXAMPLE 2

Preparation of antibiotic deglucoteicoplanin n-octyl ester, hydrochloride (a) from antibiotic L 17046

A suspension of 0.93 g of antibiotic L 17046 in 180 ml of 1 M octanolic hydrogen chloride is stirred at 70° C. for 10 h. The clear solution which forms is cooled to 15° C., 800 ml of ether is added and the solid which separates is collected, washed with ether and dried under vacuum at room temperature overnight, yielding 0.72 g of the crude ester of the title, which is dissolved in 60 ml of a mixture $CH_3OH/H_2O$ 80:20 (v/v). Water (400 ml) and 1 ml of 1 N HCl is added to this solution and the resulting cloudy mixture is extracted twice with 400 ml of ethyl acetate. The organic extracts are combined and 1 ml of 1 N HCl in 100 ml of n-butanol is added. The solution is concentrated to a final volume of about 80 ml and 100 ml of a mixture ethyl acetate/ether 3:2 (v/v) is added. The resulting cloudy solution is kept at 10° C. for 3 days. A solid separates which is collected, washed with ether and dried under vacuum at room temperature overnight, yielding 0.16 g of the n-octyl ester of the title.

(b) from antibiotic deglucoteicoplanin

A suspension of 0.7 g of deglucoteicoplanin in 40 ml of 1 M octanolic hydrogen chloride was stirred at 65° C. for 1 h. The clear solution which forms is worked up as described above, yielding 0.41 g of the n-octyl ester of the title.

Essentially following the procedure of the foregoing Example 2 a) but substituting teicoplanin, teicoplanin $A_2$ component 2, or antibiotic L 17054 for antibiotic L 17046 as the starting material, the same compound of the title is obtained in similar yields (from about 0.15 to about 0.2 g, employing the same molar amount of reactant as in the foregoing Example).

EXAMPLE 3

(A) Preparation of antibiotic deglucoteicoplanin benzyl ester, hydrochloride (a) by treatment of antibiotic L 17046 with benzyl alcohol 1 M hydrogen chloride A suspension of 18 g of essentially pure antibiotic L 17046 in 600 ml of 1 M hydrogen chloride in benzyl alcohol is stirred at 60° C. After 15 minutes a clear solution forms which is stirred for additional 3 h at the same temperature, then the solution is cooled to 15° C. and stirring is continued at room temperature for additional 12 h. By adding 4 l of a mixture n-hexane/ether 4:3 (v/v) a solid separates which is collected, washed with 1 l of ether and re-dissolved in 150 ml of methanol. The solution is diluted with 1 l of $H_2O$ and extracted (pH 2.5) twice with 2 l of ethyl acetate. The organic layers are combined and a mixture of 10 ml of 1 N HCl in 200 ml of n-butanol is added, then the solution is concentrated to a small volume. By adding 1 l of a mixture n-hexane/ether 3:2 (v/v) a solid separates which is collected, washed with ether and dried under vacuum at 40° C. for 8 h yielding 8.5 g of deglucoteicoplanin benzyl ester, hydrochloride (analysis: deglucoteicoplanin benzyl ester, hydrochloride 70%, water and solvents 15%, undefined impurities 15%).

(b) by treatment of the antibiotic L 17054 with 1 M hydrogen chloride in 90% aqueous benzyl alcohol To a stirred suspension of 10 g of essentially pure antibiotic L 17054 in 90 ml of benzyl alcohol, 10 ml of 37% hydrochloric acid is added at 40° C. The reaction mixture is heated to 70° C. and stirring is continued for 30 minutes, then water is removed under vacuum (about 20 mmHg) at 70° C. (bath temperature). Benzene is added and then the mixture is evaporated under reduced pressure to remove any aqueous residue by means of azeotropic distillation. Then the mixture is diluted with 100 ml of 1 M hydrogen chloride in aqueous benzyl alcohol (prepared as above). The clear solution so obtained is stirred at 65° C. for 6 h, then cooled to 15° C. and worked up as described in the foregoing example (Example 3b)) yielding 4.85 g of deglucoteicoplanin benzyl ester, hydrochloride (analysis: deglucoteicoplanin benzyl ester, hydrochloride 75%, water and solvents 15%, undefined impurities 10%).

(c) by treatment of teicoplanin with 2 M hydrochloric acid in 80% aqueous benzyl alcohol, under vacuum and with repeated additions of benzene and 37% hydrochloric acid.

To a stirred suspension of 10 g of essentially pure teicoplanin in 80 ml of benzyl alcohol, 20 ml of 37% hydrochloric acid is added at 40° C. The mixture is kept under vacuum (about 20 mmHg) for about 60 minutes while heating to about 65° C. (bath temperature), then 50 ml of benzene is added and the mixture is evaporated under vacuum at about 65° C. After 30 minutes, a mixture of 5 ml of 37% hydrochloric acid in 25 ml of benzyl alcohol is added to the reaction mixture which is then re-submitted to the "under vacuum" procedure (about 20 mmHg; about 65° C.) for 30 minutes. Then 50 ml of benzene is added and evaporated as previously described. Alternate additions of mixtures of 5 ml of 37% hydrochloric acid in 15 ml of benzyl alcohol and of 50 ml of benzene separated by the "under vacuum" procedure are repeated every 30 minutes for 8 hours. Then 20 ml of 37% hydrochloric acid and 100 ml of benzene are added, while water and benzene are evaporated under vacuum and the resulting clear solution is stirred at room temperature and pressure under argon atmosphere for 12 h, then the reaction mixture is poured into 1.5 l of ether. A solid separates which is collected, washed with ether and dried under vacuum at room temperature overnight, yielding 10 g of the crude ester of the title. This product is dissolved in 150 ml of methanol and 300 ml of water and 300 ml of ethyl acetate are added thereto with vigorous stirring. After few minutes additional 300 ml of water, 300 ml of ethyl acetate and a mixture of 300 ml of n-butanol/water 1:2 (v/v) were added. The pH of the aqueous layer is adjusted to 3.5 and the organic phase is separated. The aqueous phase is extracted twice with ethyl acetate (600 ml each time). The organic layers are combined, washed with 400 ml of water and concentrated to a small volume under vacuum. By adding ether a solid separates which is collected, washed with ether and dried under vacuum at room temperature overnight, yielding 6.1 g of crude deglucoteicoplanin benzyl ester, hydrochloride (analysis: deglucoteicoplanin benzyl ester, hydrochloride 75%; water and solvents 15%, undefined impurities 10%).

(B) Purification of deglucoteicoplanin benzyl ester by silica-gel column chromatography Silica-gel 60 (0.06–0.2 mm Merck) (10 g) is added to a solution of 2.5 g of crude deglucoteicoplanin benzyl ester (titre 65%) in 100 ml of 90% aqueous methanol. The solvent is completely evaporated under vacuum and the residue is applied to a chromatographic column containing 250 g of silica-gel slurried in acetonitrile ($CH_3CN$).

The column is developed by sequentially using the following solvent mixtures:

| | |
|---|---|
| $CH_3CN$ | 250 ml |
| $CH_3CN/H_2O$ 97:3 (v/v) | 500 ml |
| $CH_3CN/H_2O$ 94:6 (v/v) | 500 ml |

The eluates are discarded, then the column is eluted with a linear gradient of acetonitrile in water obtained by mixing 1.5 l each of the solvent mixtures $CH_3CN/H_2O$ 94:6 (v/v) and $CH_3CN/H_2O$ 70:30 (v/v) at a rate of 200 ml/h. Fractions of 25 ml are collected and assayed by HPLC. Deglucoteicoplanin benzyl ester containing fractions are combined (700 ml), n-butanolic 0.05 M hydrogen chloride (250 ml) is added thereto, and the solvents are evaporated up to a final volume of about 30 ml. By adding ether (300 ml) a solid separates which is collected, washed with ether and dried under vacuum at 40° C. for 48 h, yielding 1.6 g of essentially pure deglucoteicoplanin benzyl ester hydrochloride.

Essentially following the procedure of the foregoing Example 3 a) but substituting teicoplanin, teicoplanin $A_2$ component 2, deglucoteicoplanin, or antibiotic L 17054 for antibiotic L 17046 as the starting material, the same compound of the title is obtained in similar yields, (employing the same molar amount of reactant as in the foregoing Example).

The compound of the title is also obtained starting from a material selected from teicoplanin $A_2$ component 2, antibiotic L 17046 or deglucoteicoplanin and essentially following the procedure of examples 3 b) or c) with substantially the same yields as exemplified above.

EXAMPLE 4

N-benzyloxycarbonyl deglucoteicoplanin (N-CBZ deglucoteicoplanin)

A solution of 0.45 ml of benzylchloroformate in 10 ml of acetone is added dropwise to a stirred solution of 2.5 g of deglucoteicoplanin and 0.5 g of sodium bicarbonate in 150 ml of the mixture water/acetone 1:2 (v/v) at 0°–3° C. After 30 min, 500 ml of water is added and the resulting solution is extracted with 500 ml of ethyl ether. The organic layer is discarded while the aqueous phase is adjusted to pH 3.5 with 1 N HCl and extracted with 600 ml of the mixture ethyl acetate/n-butanol 2:1 (v/v). The organic layer is separated, washed with 200 ml of water, and then concentrated to a small volume under reduced pressure. By adding ethyl ether, a solid separates which is collected, washed with ether and dried under vacuum at 40° C. overnight, yielding 2.7 g of essentially pure N-benzyloxycarbonyl deglucoteicoplanin.

EXAMPLE 5

N-benzyloxycarbonyl deglucoteicoplanin, pivaloyloxymethyl ester

To a stirred solution of 0.7 g of N-benzyloxycarbonyl deglucoteicoplanin in 20 ml of dimethylformamide, 0.1 ml of triethylamine (TEA), 0.1 ml of chloromethyl pivalate and 35 mg of sodium iodide are added at room temperature. The reaction mixture is heated to 45° C. for 4 h, and then further 0.1 ml of TEA and 0.15 ml of chloroethyl pivalate are added. After keeping this mixture about 4 h at 45° C. and overnight at room temperature, additional 0.1 ml of TEA and 0.1 ml of chloroethyl pivalate are added. This mixture is then stirred for about 24 h at room temperature then 400 ml of ether are added with vigorous stirring. The oily compound which separates is treated with 200 ml of the mixture acetone/ether 1:9 (v/v), then collected, washed with ether and dried overnight under vacuum at room temperature, yielding 0.72 g of crude N-benzyloxycarbonyl deglucoteicoplanin pivaloyloxymethyl ester. This product is enough pure to be submitted to the deprotection reaction.

A sample is purified by silicagel column chromatography eluting with a liner gradient of methylene chloride/methanol from 95:5 to 50:50 (v/v) and its analytical data are reported in Tables I–III.

EXAMPLE 6

Deglucoteicoplanin pivaloyloxymethyl ester (a) To a solution of 1.6 g of crude N-benzyloxycarbonyl deglucoteicoplanin pivaloyloxymethyl ester obtained according to the foregoing Example 5 in 400 ml of methanol, 1.2 g of 5% palladium on carbon is added. The resulting suspension is submitted to hydrogenolysis at room temperature and ambient pressure. After 30 min, about 96 ml of hydrogen is absorbed. The reaction is completed. The catalyst is filtered off, washed with 600 ml of the mixture methanol/0.1 N HCl 8:2 (v/v), and discarded. To the pooled filtrate 400 ml of n-butanol is added and the resulting solution is concentrated to a small volume under reduced pressure. By adding ethyl ether a solid separates which is collected, washed with ether and dried under vacuum at room temperature overnight, obtaining 1.33 g of crude deglucoteicoplanin pivaloyloxymethyl ester.

(b) Purification of deglucoteicoplanin pivaloyloxymethyl ester

The product obtained according to the foregoing Example 6a) (1.33 g) is dissolved in 100 ml of the mixture methanol/acetonitrile 15:85 (v/v) and the resulting solution is applied to a column of 300 g of silicagel 60 Merck (0.06–0.20 mm;) in acetonitrile. The column is sequentially developed with 500 ml each of the following solvent mixtures $CH_3CN/CH_3OH$ 90:10, 85:15, 80:20, 75:25, 70:30 and 65:35 (v/v), while collecting fractions of 150 ml each at the rate of 450 ml/h. The product containing fractions (fractions 14 to 19) are pooled, n.butanolic 0.05 M hydrogen chloride is added, and the solvents are evaporated at 35° C. under vacuum to a final volume of ~150 ml. The solid which separates is collected, washed with ethyl ether and dried under vacuum at room temperature overnight, obtaining 0.44 g of essentially pure antibiotic deglucoteicoplanin pivaloyloxymethyl ester, hydrochloride.

EXAMPLE 7

N-benzyloxycarbonyl deglucoteicoplanin ethyl ester

N-benzyloxycarbonyl deglucoteicoplanin obtained according to Example 4 (1 g) is dissolved in dimethylformamide (30 ml) and finely powdered potassium carbonate (70 mg) is added thereto. The mixture is stirred until a solution is obtained, then ethyl bromide (0.2 ml) is added. The mixture is stirred at room temperature until the reaction is completed then the reaction mixture is poured in water (500 ml) and the pH is adjusted to about 8 with potassium bicarbonate. This mixture is extracted with ethyl acetate (3×300 ml) and the organic phase is pooled, washed with water and concentrated to dryness under reduced pressure. The residue is dissolved in ethyl acetate (50 ml) and the reaction product is precipitated by adding ethyl ether. When the precipitation is completed, the solid is recovered by filtration and dried yielding 0.8 g of N-benzyloxycarbonyl deglucoteicoplanin ethyl ester

EXAMPLE 8

Deglucoteicoplanin ethyl ester

N-benzyloxycarbonyl deglucoteicoplanin ethyl ester (544 mg) obtained according to the foregoing example is dissolved in ethanol (5 ml). To this solution, 5% palladium on carbon (50 mg) is added. Hydrogen is bubbled in the stirred mixture at ambient pressure and temperature.

When the reaction is completed, the reaction mixture is filtered, the collected catalyst is washed with ethanol and discarded, and ethyl ether (200 ml) is added to the pooled ethanolic solution A precipitate forms which is collected by filtration and dried in the air yielding 450 mg of a whitish product which is deglucoteicoplanin ethyl ester.

EXAMPLE 9

Preparation of deglucoteicoplanin 4-chloro-butyl ester

Dry hydrochloric acid is bubbled into a stirred suspension of 10 g (about 5.4 mmol) of teicoplanin in 400 ml of dry tetrahydrofuran while maintaining the temperature at 45°-50° C. After 36 h the resulting solution is concentrated to a small volume under reduced pressure at 35° C., then ether is added and the solid which separates is collected, washed with ether and re-dissolved in 1 l of a mixture acetonitrile:water 20:80 (v/v). The resulting solution is loaded on a column containing 0.6 kg of silanized silica gel (0.06-0.2 mm) Merck prepared in 0.2% aqueous ammonium formate. The column is developed with a linear gradient from 30 to 90% $CH_3CN$ in $H_2O$ in 20 h at a rate of about 300 ml/h, while collecting 20 ml fractions. The fractions containing the compound of the title are pooled, n-butanol (v/v) is added and the solvents are evaporated under vacuum at 45° C. The solid residue is triturated with ether, then it is collected, washed with ether and dried in vacuo at 40° C. overnight, yielding 3.2 g of pure compound of the title, as free base.

EXAMPLE 10

Preparation of N-BOC deglucoteicoplanin

To a stirred solution of deglucoteicoplanin hydrochloride (1.25 g, 1 mmole) in DMF (20 ml) 2,4,5-trichloro-t-butylcarbonate (340 mg, 1.1 mmole, Janssen) and triethylamine (0.7 ml) are added. The mixture is kept overnight at room temperature then water (200 ml) is added and the pH is adjusted to pH 2 by adding N HCl. The product is extracted with 150 ml of ethylacetate:n-butanol 3:1 (v/v). The organic layers are collected and concentrated to about 40 ml; then ether (250 ml) is added. The suspension, after standing overnight at 0° C., is filtered, the recovered product is washed with ether and dried in vacuo at 50° C. Yield 1.1 g of of the pure compound of the title.

EXAMPLE 11

Preparation of methyl ester of N-BOC deglucoteicoplanin

To a stirred solution of N-BOC deglucoteicoplanin (500 mg, 0.385 mmole) in DMF (10 ml), finely ground $KHCO_3$ (40 mg) and methyl iodide (30 μl) are added. The mixture is stirred at room temperature until the reaction is completed (3 hours), then water (100 ml) is added and the mixture extracted three times with n-butanol (100 ml). The organic extracts are washed with water and concentrated to 20 ml in vacuo at 50° C. The reaction product is precipitated by adding ether (200 ml). After standing overnight at 0° C., the product is collected by filtration, washed with ether and dried in vacuo at 50° C., yielding 320 mg of the compound of the title.

EXAMPLE 12

Preparation of deglucoteicoplanin methyl ester, trifluoroacetate salt

Methyl ester of N-BOC deglucoteicoplanin as obtained above is stirred with 2 ml of trifluoroacetic acid. After 30 minutes the product is precipitated by adding ether, filtered, washed with ether and dried. Yield 300 mg of the compound of the title.

EXAMPLE 13

Preparation of N-BOC deglucoteicoplanin 2-(N-morpholinyl)ethyl ester

In a flask equipped with a magnetic stirrer and a drying valve, N-BOC deglucoteicoplanin (430 mg, 0.331 mmole), $KHCO_3$ (132.5 mg, 1.32 mmole) and N-(2-chloroethyl)-morpholine hydrochloride (123.1 mg, 0.662 mmole) are dissolved successively in DMF (4 ml). The solution is stirred at room temperature for 50 h, then further 60 mg of N-(2-chloroethyl)-morpholine hydrochloride and 30 mg of $KHCO_3$ are added, continuing the reaction for additional 15 h. The reaction mixture is diluted with water (30 ml) and extracted with n-butanol (2×50 ml). The organic layers are pooled and evaporated in vacuo at 50° C. The residue is treated with 100 ml of ether, collected and dried in the air, yielding 450 mg of crude compound of the title which is purified by "flash chromatography" on 100 g of silicagel (230-400 mesh, Merck) eluting with a mixture of $CH_2Cl_2$/MeOH/$NH_3$ 37% - 80:20:1. The fractions containing the pure product are pooled and evaporated in vacuo. The solid residue is treated with ether, filtered and dried in the air yielding 150 mg of the compound of the title.

EXAMPLE 14

Preparation of deglucoteicoplanin 2-(N-morpholinyl)ethyl ester, bis-trifluoroacetate N-BOC deglucoteicoplanin 2-(N-morpholinyl)-ethyl ester (150 mg), prepared as described above, is suspended in $CH_2Cl_2$ (1 ml) and 1 ml of trifluoroacetic acid is added with stirring. After 20 minutes the mixture is diluted with ethyl ether (60 ml) and the solid, after standing for 30 minutes, is collected, washed with ether and dried in vacuo at 50° C. overnight. Yield 150 mg of the compound of the title.

EXAMPLE 15

Preparation of N-BOC deglucoteicoplanin 2-hydroxyethyl ester

N-BOC deglucoteicoplanin (450 mg, 0.346 mmole) is dissolved in 5 ml of DMF, successively $KHCO_3$ (105 mg, 1.05 mmole) and 2-bromoethanol (430 mg, 3.46 mmole) are added, then stirring is continued at room temperature overnight. $KHCO_3$ (50 mg) is added again and then the mixture is kept at 50° C. for 4 hours. The suspension is cooled, diluted with water (60 ml) and extracted with n-butanol (2×50 ml), then the organic phases are pooled, washed with water and concentrated in vacuo at 50° C. The residue, dissolved in 1 ml of methanol is precipitated by adding 100 ml of ether. The product is filtered, washed with ether and dried in the air yielding 455 mg of the crude compound of the title which is purified through a "flash chromatography column" containing 60 g of Lichroprep RP-8 (40–63 μm Merck) prepared in $H_2O$/acetonitrile 90:10. The column is developed with a linear gradient from 10 to 40% of $CH_3CN$ in water at 0.5 atmosphere pressure, collecting 15 ml fractions. Fractions containing the pure compound are pooled, additioned with n-butanol (v/v) and the solvent evaporated under vacuum at 50° C. The residue is triturated with ether, filtered and dried in vacuo at 50° C. yielding 190 mg of pure compound of the title.

EXAMPLE 16

Preparation of deglucoteicoplanin 2-hydroxyethyl ester, trifluoroacetate

N-BOC deglucoteicoplanin 2-hydroxyethyl ester (190 mg), obtained as above described, is suspended in 1 ml of $CH_2Cl_2$ and under stirring 1 ml of $CF_3COOH$ is added. After 10 minutes, the solvent is evaporated and the residue is triturated with ether, filtered, washed with ether and dried in vacuo at 50° C. overnight. Yield 155 mg of pure compound of the title.

EXAMPLE 17

Preparation of deglucoteicoplanin N-benzyloxycarbonyl, 2-bromoethyl ester

N-CBZ-deglucoteicoplanin (1.5 g) is dissolved in 50 ml of DMF. To this solution $KHCO_3$ (150 mg) and 1,2-dibromoethane (1 ml) are added then the mixture is stirred 25 h at room temperature. The reaction mixture is dripped in 900 ml of ethyl ether then the solid formed is filtered, washed with ether and dried in the air, yielding 1.5 g of crude material. This material is dissolved in the minumum amount of MeOH and diluted with ethyl acetate (500 ml); the organic solution is washed with 500 ml of water containing NaHCO (0.5 g) and NaCl (1.5 g). The organic phase is added with some n-butanol and concentrated to 10 ml; ethyl ether is added and the solid filtered, washed and dried under vacuum at 50° C. Yield 1.2 g of pure compound of the title.

EXAMPLE 18

Preparation of deglucoteicoplanin 2-bromoethyl ester, hydrochloride

Deglucoteicoplanin N-benzyloxycarbonyl, 2-bromoethyl ester (1 g), prepared according to the above Example, is dissolved in a mixture of N HCl (30 ml) and MeOH (120 ml). To this solution 5% Palladium on $BaSO_4$ (1 g) is added. Hydrogen is bubbled in the stirred mixture at ambient pressure and temperature. When hydrogenation is completed (3 h), the reaction mixture is filtered, the collected catalyst is washed with methanol (150 ml) and discarded, silanized silicagel 60 (10 g, Merck) is added and the mixture evaporated to dryness under vacuum. The solid residue is loaded on the top of a column containing 250 g of the same silicagel, prepared in $H_2O$/$CH_3CN$ 75:25 by volume. The column is developed with a linear gradient from 25 to 70% of $CH_3CN$ in $H_2O$ while collecting 20 ml fractions. Fractions containing the pure compound of the title are pooled, n-butanol (v/v) is added and the solvents are evaporated under vacuum at 45° C., the solid residue is triturated with ether, then it is collected by filtration, washed with ether and dried in vacuo at 40° C. overnight. Yield 100 mg of the compound of the title.

EXAMPLE 19

Preparation of deglucoteicoplanin N-benzyloxycarbonyl, 2-fluoroethyl ester

To a solution of N-CBZ-deglucoteicoplanin (1.5 g, 1 mmole) in 50 ml of DMF, $KHCO_3$ (150 mg, 1.5 mmole) and 1-bromo-2-fluoroethane (0.2 ml, 2.68 mmole) are successively added.

The mixture is stirred at room temperature for 48 h, then it is poured in a solution of 600 ml of ethyl ether and 300 ml of hexane. The precipitate is filtered, washed with ether and dried in the air, yielding 1.75 g of crude product. This is dissolved in the minimum amount of MeOH and poured in 500 ml of ethyl acetate, then the organic solution is washed first with 500 ml of water containing $NaHCO_3$ (1 g) and NaCl (5 g) then with pure water (200 ml). The organic phase is diluted with n-butanol (100 ml) and evaporated under vacuum to a final volume of about 20 ml. By adding ether a solid separates which is collected, washed with ether and dried in the air yielding 1 g of semi-pure compound. The purification is performed on a column containing 250 g of silanized silicagel 60 (Merck) prepared in $CH_3CN$ 35% in water. The column is developed with 4 l of linear gradient from 35 to 55% of $CH_3CN$ in water collecting 20 ml fractions. Fractions containing the pure compound of the title are pooled, n-butanol (v/v) is added and the solvents are evaporated under vacuum at 45° C. The residue is triturated with ether, filtered, washed and dried in vacuo at 45° C. overnight. Yield 0.5 g of pure compound of the title.

EXAMPLE 20

Preparation of deglucoteicoplanin 2-fluoroethyl ester, hydrochloride

N-benzyloxycarbonyl deglucoteicoplanin-2-fluoroethyl ester (400 mg) obtained according to the method above described, is dissolved in 50 ml of 0.1 N HCl/MeOH 3:7 (v/v) and 400 mg of 5% Palladium on $BaSO_4$ are added. The resulting suspension is submitted to hydrogenolysis at room temperature and ambient pressure. After 2 hours the catalyst is filtered off, washed with 50 ml of MeOH and discarded. The organic solvents are pooled and silanized silicagel 60 (5 g) is added thereto. After appropriate stirring, the solvent is stripped off under vacuum and the residue is loaded on the top of a chromatographic column prepared with 50 g of silanized silicagel 60 prepared in $CH_3CN$ 5% in water at pH 3. The column is developed with one liter of a linear gradient from 5 to 25% of $CH_3CN$ in water at pH 3 (HCl 10%), collecting 20 ml fractions. Fractions containing the pure compound of the title (36–70) are pooled, n-butanol (v/v) is added and the solvents are evaporated under vacuum at 45° C. The residue is triturated with ether, then it is collected, washed and dried in vacuo at 40° C. overnight, yielding 50 mg of pure compound of the title.

EXAMPLE 21

Preparation of deglucoteicoplanin 2-bromoethyl ester, hydrochloride via "N-salicyliden" protection To a solution of deglucoteicoplanin (3 g, 2 mmole) in 50 ml of DMF, salicylaldehyde (0.5 ml, 4.7 mmole) is added and the solution is stirred 24 hours at room temperature. The mixture is poured into 500 ml of ether and the precipitate is collected and washed with ether. The N-salicyliden deglucoteicoplanin so obtained, is dissolved in 100 ml DMF, $KHCO_3$(300 mg) and 1,2-dibromoethane (2 ml) are added. The mixture is stirred 18 hours at room temperature then it is poured in a solution of ether (1.5 l) and n-hexane (0.5 l). The solid which precipitates, is collected by filtration, washed with ether and dissolved in 50 ml of MeOH This solution is diluted with ethyl acetate (500 ml) and washed with water (2×0.5 l). The organic phase is separated, n-butanol is added and the solvents are evaporated to about 30 ml, then ether is added. The solid which precipitates is collected, washed with ether and dried in the air. Yield 3 g of crude N-salicyliden deglucoteicoplanin 2-bromoethyl ester. By purification of this product on a column containing 300 g of silicagel prepared in $CH_2Cl_2$ and developing with a gradient 1/15% MeOH in $CH_2Cl_2$ while collecting 20 ml fractions, is obtained first N-salicyliden ester and then the compound of the title. (This product shows the same $t_R$ in HPLC analysis of the compound prepared according to Example 18).

The I.R., N.M.R. and Mass data are in agreement with the structure given for the compounds of the above Examples 1-20.

We claim:

1. An ester derivative of deglucoteicoplanin of the formula

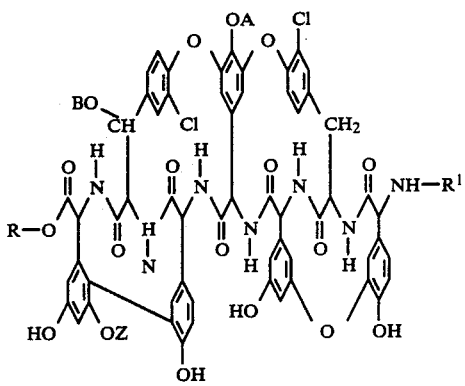

wherein
R represents a methyl or ethyl group, a benzyl group, a hydroxy ($C_1$-$C_4$)alkyl group, or a halo($C_1$-$C_4$)alkyl group
$R_1$ represents hydrogen or an amino-protecting group,
A, B, and Z each individually represent a hydrogen group or a pharmaceutically acceptable acid addition salt thereof.

2. An ester derivative of deglucoteicoplanin of claim 1 wherein $R_1$ is a hydrogen.

3. An ester derivative of deglucoteicoplanin of claim 1 wherein R represents a methyl or ethyl group, a benzyl group, a hydroxymethyl or hydroxyethyl group, or a halomethyl or haloethyl group.

4. An ester derivative of deglucoteicoplanin of claim 3 wherein $R_1$ is hydrogen.

5. An ester derivative of deglucoteicoplanin of claim 1 wherein R represents a benzyl, methyl, hydroxyethyl, bromoethyl, chloroethyl, or fluoroethyl group.

6. An ester derivative of deglucoteicoplanin of claim 5 wherein $R_1$ is hydrogen.

7. An ester derivative of deglucoteicoplanin of claim 1 wherein R represents a methyl group and $R_1$ represents a hydrogen.

8. An ester derivative of deglucoteicoplanin of claim 1 wherein R represents a benzyl group and $R_1$ represents a hydrogen.

9. An ester derivative of deglucoteicoplanin of claim 1 wherein R represents a hydroxyethyl group and $R_1$ represents a hydrogen.

10. An ester derivative of deglucoteicoplanin of claim 1 wherein R represents a bromoethyl group and $R_1$ represents a hydrogen.

11. An ester derivative of deglucoteicoplanin of claim 1 wherein R represents a chloroethyl group and $R_1$ represents a hydrogen.

12. An ester derivative of deglucoteicoplanin of claim 1 wherein R represents a fluoroethyl group and $R_1$ represents a hydrogen.

13. An antibacterial pharmaceutical composition comprising an antibacterially effective amount of a compound of one of claim 1-12 in admixture with a pharmaceutically acceptable carrier.

14. A method of treating a bacterial infection in a patient in need thereof which comprises administering to the patient an effective amount of a compound of one of claims 1-12.

15. An animal growth promotant composition which comprises an animal growth promotant effective amount of a compound of one of claims 1-12 in admixture with an animal feed composition.

* * * * *

UNITED STATES PATENT AND TRADEMARK OFFICE
CERTIFICATE OF

PATENT NO. : 4,954,483
DATED : September 4, 1990
INVENTOR(S) : Adriano Malabarba, Paolo Strazzolini, Aldo Trani, Ambrogio Magni and Bruno Cavalleri It is certified that error appears in the above-identified patent and that said Letters Patent is hereby corrected as shown below:

At Column 12, Line 4 the patent reads "follows:  of" and should read "follows:  samples of"

At Column 12, Line 24 the patent reads "NaH" and should read "NaH$_2$PO$_4$"

At Column 15, Line 10 the patent reads "0" and should read "20"

At Column 18, Line 16 the patent reads "(D$_{1cm}$" and should read "(E$_{1cm}$"

At Column 19, Line 9 the patent reads "characteristics" and should read "characteristics:"

At Column 29, Line 52 the patent reads "NaHCO" and should read "NaHCO$_3$"

At Column 31, Line 35 the patent reads "MeOH This" and should read "MeOH. This"

At Claim 13, Line 58 the patent reads "claim" and should read "claims"

Signed and Sealed this

Ninth Day of June, 1992

*Attest:*

DOUGLAS B. COMER

*Attesting Officer*    Acting Commissioner of Patents and Trademarks